US008494627B2

(12) United States Patent
Bikson et al.

(10) Patent No.: US 8,494,627 B2
(45) Date of Patent: Jul. 23, 2013

(54) NEUROCRANIAL ELECTROSTIMULATION MODELS, SYSTEMS, DEVICES, AND METHODS

(75) Inventors: Marom Bikson, Brooklyn, NY (US); Abhishek Datta, New York, NY (US); Lucas C. Parra, Broooklyn, NY (US); Jacek Dmochowski, Wechawken, NJ (US); Yuzhuo Su, New York, NY (US)

(73) Assignee: Research Foundation of the City University of New York, New York, NY (US)

( * ) Notice: Subject to any disclaimer, the term of this patent is extended or adjusted under 35 U.S.C. 154(b) by 0 days.

(21) Appl. No.: 13/294,994

(22) Filed: Nov. 11, 2011

(65) Prior Publication Data

US 2012/0265261 A1    Oct. 18, 2012

Related U.S. Application Data

(63) Continuation-in-part of application No. 13/264,142, filed as application No. PCT/US2010/030943 on Apr. 13, 2010.

(60) Provisional application No. 61/168,859, filed on Apr. 13, 2009.

(51) Int. Cl.
 *A61N 1/08*    (2006.01)

(52) U.S. Cl.
 USPC ............................................................ 607/2

(58) Field of Classification Search
 None
 See application file for complete search history.

(56) References Cited

U.S. PATENT DOCUMENTS 8,195,300 B2 *   6/2012   Gliner et al. .................... 607/45

* cited by examiner

*Primary Examiner* — Carl H Layno
*Assistant Examiner* — Paula J Stice
(74) *Attorney, Agent, or Firm* — Hoffmann & Baron, LLP

(57) ABSTRACT

Methods, systems, and apparatus, including computer programs encoded on a computer storage medium, for developing transcranial electrical stimulation protocols are disclosed. In one aspect, a method includes forming a first array of electrodes and optimizing a plurality of electrode parameters within the first array of electrodes to achieve a desired physiological response; identifying one or more electrodes within the optimized first array that have relatively low current compared to the remaining electrodes in the first array; removing the identified low current electrodes from the first array to form a second array of electrodes, wherein the number of electrodes in the second array is less than the number of electrodes in the first array and optimizing a plurality of electrode parameters with the second array of electrodes to achieve a desired physiological response.

11 Claims, 18 Drawing Sheets

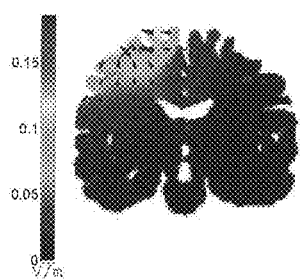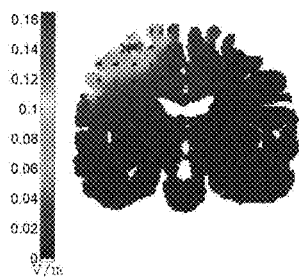
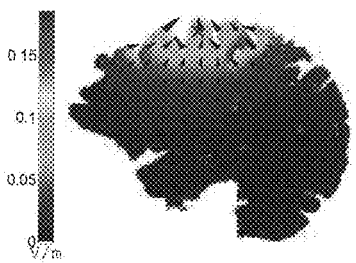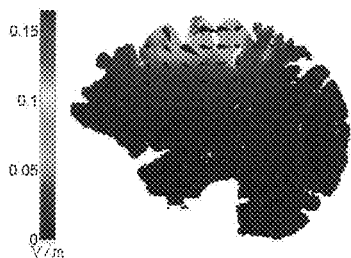
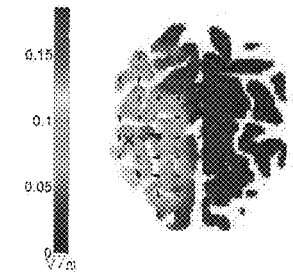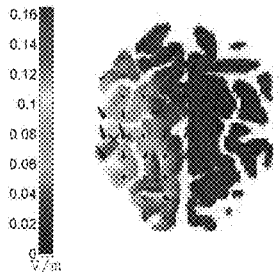
(a) Radial target: max focality.  (b) Tangential target: max focality
FIG. 11a  FIG. 11b

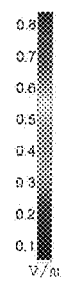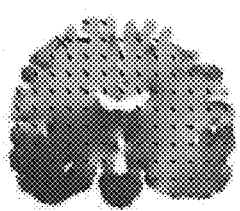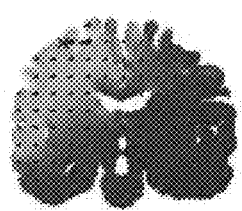
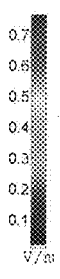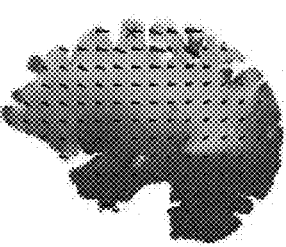
(c) Radial target: max intensity     (d) Tangential target: max intensity
FIG. 11c          FIG. 11d

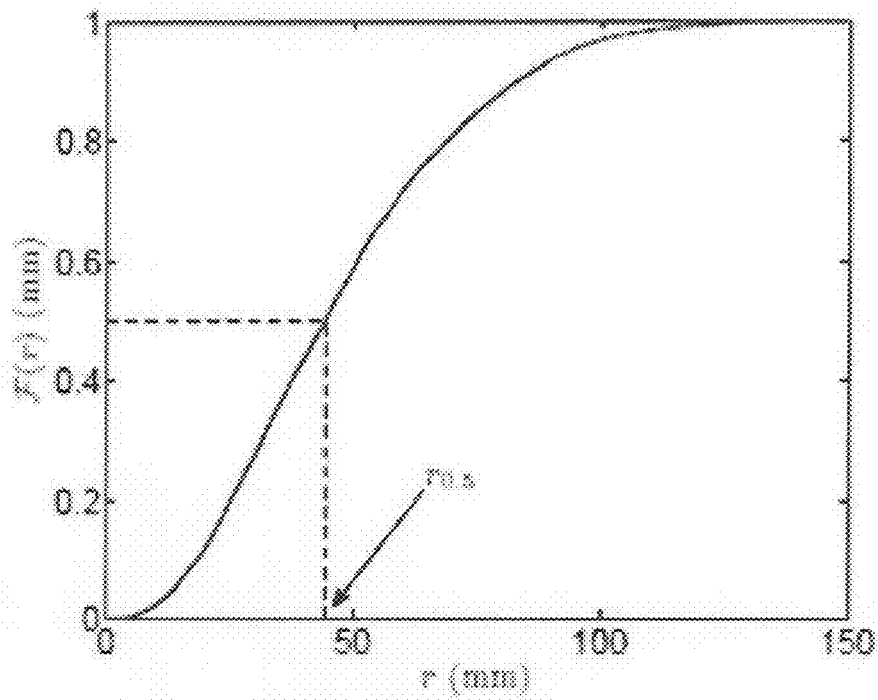
(a) Half-max radius (max focality, radial).
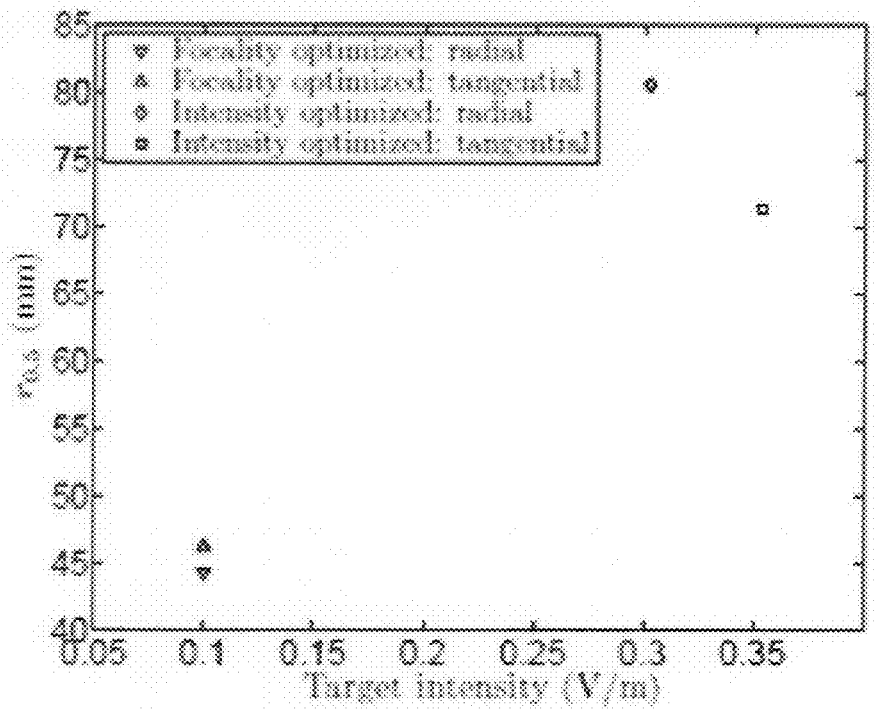
(b) Performance in the focality-intensity space.
Fig. 12a
Fig. 12b

NEUROCRANIAL ELECTROSTIMULATION MODELS, SYSTEMS, DEVICES, AND METHODS

CROSS-REFERENCE TO RELATED APPLICATIONS

This application is a continuation-in-part of U.S. patent application Ser. No. 13/264,142 which in turn claims the benefit under 35 U.S.C. §119(e) of U.S. Patent Application No. 61/168,859, entitled "Neurocranial Electrostimulation Models, Systems, Devices and Methods," filed Apr. 13, 2009, both of which are incorporated herein by reference in their entirety.

BACKGROUND

This specification generally relates to a method and apparatus of electrostimulation of body tissue, including methods of transcranial electrostimulation. For example, plastic changes in brain function can be safely induced in humans by low-intensity electrical stimulation through scalp electrodes. Such electrical stimulation is known as transcranial electrostimulation (TES). These changes can be potentially used for therapeutic or performance enhancing applications. Currently available devices are rudimentary in the sense that they do not target brain modulation and do not apply insights from biophysical studies to functionally target brain function. Moreover, current methods of TES targeting require costly and time consuming computations in order to alter treatment methods.

SUMMARY

This specification describes systems and methods relating to electrostimulation of body tissue including methods relating to electrostimulation of transcranial tissue.

In general, one innovative aspect of the subject matter described in this specification can be embodied in methods that include the actions of obtaining a model image of target tissue, developing a forward model of the electric field induced in the target tissue based on electrode configurations and tissue properties, and determining from this forward model the optimal stimulation parameters using a least squares approach to obtain a desired stimulation outcome. Other embodiments of this aspect include corresponding systems, apparatus, and computer programs, configured to perform the actions of the methods, encoded on computer storage devices.

In general, a minimized array of optimized electrodes can be determined by identifying all electrodes having relatively low current in a master array of electrodes. By removing all low current electrodes the total number of electrodes is reduced. By further connecting all electrodes that have relatively the same current but opposite polarity to a single current source, the number of current sources can be reduces. As such, a further optimization of the resulting array and current sources yields a small number of actual electrodes and current sources utilized on a subject.

Embodiments of the present invention include a method performed by a data processing apparatus, the method comprising the steps of forming a first array of electrodes; optimizing a plurality of electrode parameters within the first array of electrodes to achieve a desired physiological response; identifying one or more electrodes within the optimized first array that have relatively low current compared to the remaining electrodes in the first array; removing the identified low current electrodes from the first array to form a second array of electrodes, wherein the number of electrodes in the second array is less than the number of electrodes in the first array; and optimizing a plurality of electrode parameters with the second array of electrodes to achieve a desired physiological response.

Further embodiments of the present invention include a method performed by a data processing apparatus, the method comprising the steps of forming a first array of electrodes; optimizing a plurality of electrode parameters within the first array of electrodes to achieve a desired physiological response; identifying two or more electrodes within the optimized first array that have relatively equal current with opposite polarity; electrically connecting the two or more electrodes with relatively equal current and opposite polarity to the same current source; and optimizing a second plurality of electrode parameters with the first array of electrodes to achieve a desired physiological response.

A still further embodiment of the invention includes a method performed by a data processing apparatus, the method comprising the steps of forming a first array of electrodes; optimizing a plurality of electrode parameters within the first array of electrodes to achieve a desired physiological response; identifying one or more electrodes within the optimized first array that have relatively low current compared to the remaining electrodes in the first array; removing the identified low current electrodes from the first array to form a second array of electrodes, wherein the number of electrodes in the second array is less than the number of electrodes in the first array; identifying two or more electrodes within the optimized first array or the second array that have relatively equal current with opposite polarity; electrically connecting the two or more electrodes with relatively equal current and opposite polarity to the same current source; and optimizing a plurality of electrode parameters with the second array of electrodes to achieve a desired physiological response.

Another embodiment of the present invention includes a system for transcranial electrical stimulation comprising an optimized array of electrodes comprising a subset of the 10/10 system of electrodes wherein the subset has at least 1 less current source than the number of electrodes.

And yet another embodiment of the present invention includes a system for transcranial electrical stimulation comprising: a virtual first array of electrodes based on an image model of a subjects skull; a means for optimizing the virtual array of electrodes to achieve a physiological response, wherein the optimized virtual array identifies high current electrodes and low current electrodes; a second, physical array of electrodes comprising electrodes corresponding to the high current electrodes in the virtual array; and a means for optimizing the physical array of electrodes to achieve a physiological response.

A still further embodiment of the present in invention includes a method performed by a data processing apparatus, the method comprising the steps of building a computational model of the electrical stimulation of biological tissue; adding a first array of electrodes to this model; optimizing a plurality of electrode parameters within the first array of electrodes to achieve a desired physiological response in the tissue; identifying one or more electrodes within the optimized first array that have relatively low current compared to the remaining electrodes in the first array; removing the identified low current electrodes from the first array to form a second array of electrodes, wherein the number of electrodes in the second array is less than the number of electrodes in the first array; and optimizing a plurality of electrode parameters with the second array of electrodes to achieve a desired physiological response in the tissue.

Various embodiment of the present invention may include one or more of the following features. The first array of electrodes includes electrodes in a standard electrode placement system. The standard system of electrode placement is the 10/10 system, the 10/20 system, the concentric system, or the geodesic system. The second array of electrodes comprises a constraint number of electrodes less than the number of electrodes in the first array. The first array has N electrodes, the second array has M electrodes, wherein M is less than N, and the second array has K current sources, wherein K is less than M−1. The first array is optimized for at least one of focality or intensity of the physiological response. The physiological response is determined from the electrical field or current density induced within the tissue. The physiological response is at a specified location of brain tissue subjected to a defined orientation of the electrical field induced by the plurality of electrodes in the first or second arrays. Optimizing the first and second arrays is done using optimization criteria formulated as a convex optimization problem and solved with a least one of linearly constrained Least Squares minimization, weighted Least Squares, Linearly Constrained Minimum Variance, maximum magnitude with a linear-norm constrains, or a convex optimization technique.

Embodiments and aspects can include a computer program for optimization of a forward model having been obtained using finite element model (FEM) computations by changing electrode configurations or electrostimulation parameters utilizing: matrix calculations, linear matrix addition, transposition, or inversion; optimization algorithms; in particular optimization that exploits the linear relationship between currents and field intensity; for instance least-squares fits or least square minimization; linear or quadratic optimization; optimization with linear constraints; maximum power optimization; maximum focality optimization, constraints based on the number of electrodes; constraints based on the number of independent current sources; constraints based on the total current; constraints based on the current in a specific electrode; constraints that the currents in specific sets of electrodes must add to zero; current control; and/or voltage control.

An aspect of the subject matter described in this specification can be embodied in methods that include the actions of: obtaining an image of target tissue; assigning to the image tissue electrical conductance values; arranging a plurality of stimulation electrodes around the target tissue; computing, from the locations of electrodes and tissue electrical conductances, a forward model of the response of the tissue to applied currents; defining desired tissue response; optimizing one or more electrical stimulation parameters using the forward model to obtain the desired tissue response.

These and other embodiments can each optionally include one or more of the following features. The desired tissue response includes field intensities or currents in a portion of the target tissue and minimal stimulation of a second, different part of the tissue. The desired tissue response includes a change in the volume of tissue activated or a physiological response of the target tissue. The desired tissue response includes a change in the volume of tissue activated or a physiological response of tissue or muscle that is separate and different from the target tissue. The desired tissue response includes strict constraints of maximum allowable currents of field intensities at various tissue locations. The forward model is computed using a finite-element model of the tissue properties. The electrical conductance are non-isotropic and or non-uniform. The parameters altered include changing the voltage, current, activation time, location, sequence or number of electrodes. The desired response is optimized with a minimum number of electrodes. The desired response is optimized with a minimum number of current sources. The desired response is specified giving a desired orientation of induced electric fields/current density. The desired response is specified requiring maximum intensity and/or most focal stimulation. The step of optimizing a new electrical stimulation pattern adjusts the results of the forward model using least squares methodology and any of its derivative forms such as constrained least squares, penalizes least squares, ridge regression, elastic nets, linearly constrained minimum variance, etc. The step of optimizing a new electrical stimulation pattern determines a volume of tissue activated that is different than the volume of tissue activated to determine the forward model. The image is derived from a pre-existing image library or a target tissue specific image. The image is derived from a PET image, an MRI image, a CT image, or a combination of imaging techniques. The target tissue is transcranial tissue (tissue inside the skull). The electrodes comprise at least two or more electrodes. The electrodes comprise at least 10 or more electrodes. The electrodes comprise at least 100 or more electrodes. The electrodes comprise at least 200 or more electrodes. The electrodes comprise at least 256 or more electrodes. The plurality of electrodes are place around the target tissue based on anatomical landmarks. The plurality of electrodes are placed around the target tissue using the International 10-10 EEG electrode placing system or any other conventional electrode placing system. The plurality of electrodes are placed around the target tissue in a pattern on the skin, below the skin or within the target tissue. The electrical stimulation applied is a direct current of 0 to 10 mA. The electrical stimulation applied is an alternating current of 0-10 mA and 0 H-1 kHz. The electrical stimulation applied is the same for each electrode in the plurality of electrodes. The electrical stimulation applied is different for each electrode in the plurality of electrodes.

In general, another aspect of the subject matter described in this specification can be embodied in methods that include the actions of accepting an image model of target tissue; obtaining a forward model having a first electrode configuration and first electrical stimulation parameters based on electrical stimulation of the target tissue; accepting electrode configuration changes or electrical stimulation parameter changes resulting in a second electrode configuration or second electrical stimulation parameters; determining an optimized tissue model using a linear or quadratic optimization methodology and based on the second electrode configuration or second electrical stimulation parameter changes; comparing the optimized tissue model with a desired outcome; and providing a confirmation of the optimized model with the desired outcome.

Particular embodiments of the subject matter described in this specification can be implemented so as to realize one or more of the following advantages. Electrode configuration or placement of individual electrodes in the electrode configuration can facilitate: control the volume of (brain) tissue activated by neurocranial electrostimulation; determination of the volume of influence during stimulation; determination of the neurophysiological outcome of stimulation; determination of the clinical or behavioral outcome of stimulation; targeting of a specific brain region such as the cortex, a cortical region, the hippocampus, deep brain structures, axons, axons of passage, pre-frontal cortex, motor region, or sensory regions; treatment of a neurological or psychiatric disease; prevention of tissue damage or prevent cognitive side-effects; determination of the hazards of electrostimulation; accommodation of individual factors, for example to optimize treatment based on patient specific anatomical features; control of stimulation dose; triggering a specific desired response; reduction of stimulation artifact; and creation of a sham stimulation or establishing a control stimulation condition.

Particular embodiments of the subject matter described in this specification can be implemented so as to realize one or more of the following additional advantages. Specific anode/cathode relationships can be established between electrodes, such as neurocranial electrodes, to stimulate the tissue near these electrodes, such as brain tissue near the neurocranial electrodes. Electrodes and other hardware including cranial caps and circuitry can be fabricated based on an optimized model. Clinicians can determine a course of treatment or even if a treatment should proceed based on an optimized model without repeated trial and error stimulation protocols on an actual patient. Electrical stimulation systems for patient treatment can be programmed in accordance with electrode configurations and stimulation parameters identified using the optimized stimulation model. Clinicians can see multiple optimized models without having to run multiple FEM analyses; the cost of stimulation modeling, as reflected in necessary resources (computers), both manual and computational time, supplementary on-site expertise and technical help needed, financial cost, and ability to deploy the optimization in a wide range of environment are reduced. Specifically, 1) the "wait time" for stimulation optimization is reduced and optimization can be done locally by a clinician, for example on a lap-top; 2) the resulted optimized stimulation parameters are superior than those achieved with other (iterative methods) and moreover can include additional practical constraints as needed, for example minimizing skin irritation and damage or the number of electrodes and number of required current sources (robustness, simplicity, and accessibility of technology/therapy and complex stimulators can be avoided). The system and methods outlined in this advantage thus increases the safety and efficacy of Neurocranial stimulation.

The details of one or more embodiments of the subject matter described in this specification are set forth in the accompanying drawings and the description below. Other features, aspects, and advantages of the subject matter will become apparent from the description, the drawings, and the claims.

BRIEF DESCRIPTION OF THE DRAWINGS

FIGS. 11a-d illustrate optimized electrical fields for varying orientation and criterion.

FIGS. 12a-b illustrate graphical representations of stimulation results.

Like reference numbers and designations in the various drawings indicate like elements.

DETAILED DESCRIPTION

Figure 1:
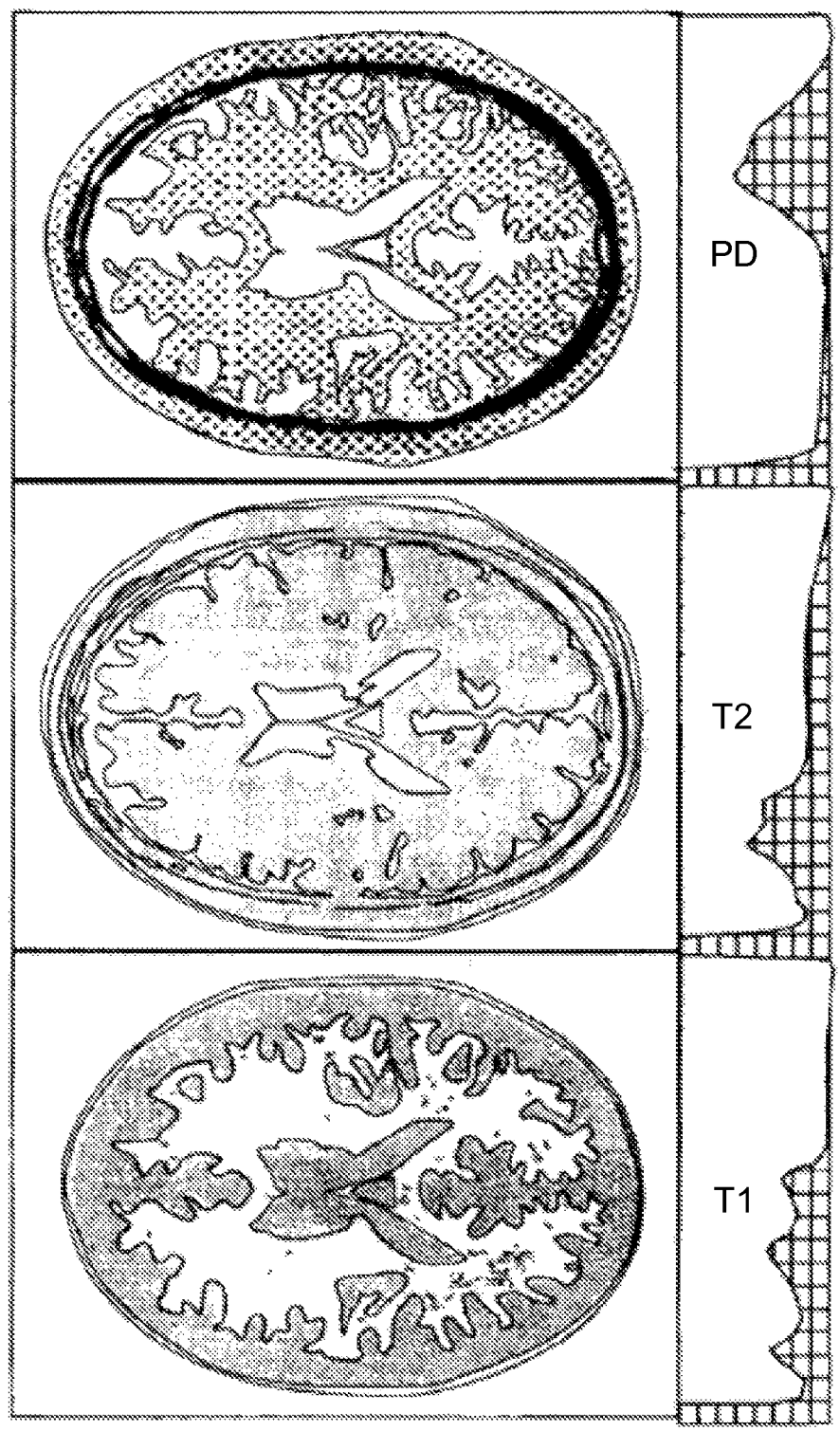
FIG. 1 is an illustration an exemplary image of target tissue.

When applying electrostimulation to body tissue, for example neurocranial electrostimulation, decisions must be made regarding the configuration of electrodes and the parameters of the electrical inputs to the electrodes in order to obtain a desired result from the electrostimulation. That is clinicians must determine (1) the positioning of electrodes (how many and where does each electrode go around the targeted tissue), and (2) how much current (or voltage) to apply to each electrode, the duration of the current (or voltage), and the sequence of the activation of electrodes with the specified current (or voltage) for the identified duration. These decisions regarding electrode configuration and stimulation parameters fundamentally affect the outcome of the electrical stimulation on the specific target tissue. One advantage of electrical stimulation is the ability to customize therapy for diseases, anatomical targets, and individuals—but at the same time the many permutations of stimulation configurations (electrode locations, current intensity) make determining an optimal, or even good, configuration challenging. This applies for positioning of electrodes in an implant, but for Neurocranial stimulation using arrays of surface electrode, of potentially high number, there are even more potential permutations. Moreover, electrode configuration and stimulation parameters have typically been determined using multiple trial and error procedures on the patient along with lengthy and costly computer analyses and modeling that are specific to each electrode configuration and stimulation parameter. Computer modeling using forward Finite Element Modeling ("FEM") analyses have been run for "generic" or standard library tissue images and data, such as generic head models. Forward FEM models have also been run based on individual head data such as measurements and MRI anatomical scans. Such FEM models reduce patient trial and error procedures but involve expansive computer simulations that are specific to each electrode configuration and stimulation parameter associated with each tissue image/model. This is costly and time consuming. Moreover, there are many permutations of potential stimulation configuration resulting in an intractable number of stimulation that would have be run iteratively—in this way an ideal configuration is unlikely to be found. Implementations of the present invention eliminate the need to repeated patient trial and error procedures or multiple matrix or FEM calculations, thereby reducing the time and cost of optimizing electrode configuration and stimulation parameters to achieve a desired outcome from an electrostimulation procedure. Moreover, the implementation in the present invention yields the best electrode configuration and currents with or without additional constraints as practically relevant to the clinical application.

Transcranial electrical stimulation provides a noninvasive tool to elicit neuromodulation by delivering current through electrodes placed on the scalp. The current clinical paradigm typically use two large electrodes (e.g. saline-soaked sponges) to inject current through the head resulting in electric fields that are broadly distributed over large regions of the brain.

Implementations of the present invention include a method that uses multiple small electrodes with independent current controls which are systematically optimized to achieve effective and targeted stimulation while enforcing safety constraints. An optimized relationship between achievable intensity (at the target tissue) and focality can be achieved using methods of the present invention.

When compared with conventional large pad-electrodes, implementations of the present invention achieve simultaneously more focal (between 50-90% and more intense (between 75-99%) stimulation of cortical targets using the same total current applied. These improvements exploit the previously unrecognized and non-trivial dependency of the optimal electrode configuration on the safety constraint and desired field orientation. Similarly, by exploiting idiosyncratic differences in brain anatomy, the optimization approach improves on previous un-optimized approaches using small electrodes (focality/intensity of about 25%/63% improvement over simple bi-polar and about 47%/97% improvement over the 4×1 electrode configuration).

It has been found that the optimal use of conventional bipolar configurations: maximally intense tangential fields are attained with the two electrodes placed at a considerable distance from the target along the direction of the desired field; when radial fields are desired, the maximum intensity configuration consists of a single electrode placed directly over the target with a distant return electrode. As such, if a target location and stimulation orientation can be defined by a clinician then the approaches of various embodiments of the present invention provide improved focality and intensity as compared previous solutions resulting in improved patient safety and increased clinical efficacy.

Transcranial direct current stimulation (tDCS) is an emerging neurotechnology involving the application of small direct currents to the surface of the scalp to elicit modulation of neural activity. tDCS can be a therapeutic tool for a wide array of neurological conditions, including major depression, craving cessation, pain management, epilepsy, Parkinson's disease, and motor and speech rehabilitation after stroke. Moreover, tDCS can improve cognitive function, specifically memory in healthy subjects.

In comparison to other brain stimulation modalities such as deep brain stimulation, electroconvulsive therapy (ECT) or transcranial magnetic stimulation, the electric fields produced by tDCS are small, about 1 V/m or less for tDCS as compared to approximately 100 V/m for other modalities. It should be noted, however, that while the resulting of membrane polarization of individual cells is weak, incrementally polarizing a large population of interconnected neurons significantly alters network dynamics.

tDCS also offers practical advantages over other methods of brain stimulation. These advantages include a simplified apparatus or kit comprising at least a pair of electrodes, a battery and a relatively simple circuit for injecting a controlled current intensity a the stimulating electrode while drawing an equivalent return current at the reference electrode. tDCS is an inexpensive procedure, well-tolerated by the subject, flexible in its administration, with effects lasting well beyond the duration of the stimulation.

Two factors previously hindering the rational clinical deployment of tDCS have been the limited stimulation intensities and difficulty in precisely focusing the stimulating electric fields. A significant fraction of the injected current is shunted through the scalp, thus bypassing the brain all together and limiting the intensity of the electric field in the target region. Additionally, a lack of focal stimulation results form the diffusion of the current through the highly conducive cerebrospinal fluid (CSF). High-resolution computational models show that CSF conducts currents to "hot-spots" that depend on the specific anatomy of the skull and idiosyncratic folding of the brain and which are not immediately apparent form the location of the electrodes on the scalp.

Aspects of the present invention relate to the speed of optimization and the feasibility of optimization of a matrix solution of a particular electrode configuration having a particular stimulation parameter (current or voltage intensity). The invention rests on the central observation that electric-field are related to the applied currents as a simple linear equation (matrix vector multiplication). Hence, optimization exploiting this linear relationship is much improved in speed and flexibility in terms of desired optimization criteria. Prior art which does not realize this relationship is hampered by an intractable optimization problem, does not find optimal solutions, and is severely limited by which optimization criterion to use. See e.g., C. W. Im, H. H. Jung, J. D. Choi, S. Y. Lee, and K. Y. Jung, "Determination of optimal electrode positions for transcranial direct current stimulation," Physics in Medicine and Biology, 53, pp. N219-N225, 2008. Ji-Hye Park; Do-Won Kim; Chang-Hwan Im; A novel array-type transcranial direct current stimulation (tDCS) system for accurate focusing on targeted brain regions" Electromagnetic Field Computation (CEFC), 2010 14th Biennial IEEE Conference on, 9-12 May 2010, all of which are incorporated herein by reference in their entirety.

In one aspect, a series of models are run that calculate the electric field response in the target tissue when one electrode of a plurality of electrodes in an electrode configuration is stimulated at a given current or voltage intensity. In one embodiment, the reference electrode in each case may be an additional fixed electrode or set fixed point in the tissue. In another embodiment, the solutions are from a set of pairs. This model is repeated for each electrode position in the plurality of electrodes in the electrode configuration surrounding the target tissue, (e.g., 100 electrode positions=100 simulations). The same stimulation parameter (e.g., voltage or current intensity) is used for each of run electrode or distinct stimulation parameters are run for each electrode. Regardless, generally only a single stimulation parameter is run for each electrode. Modeling each electrode in the electrode configuration in this manner results in a "forward-model" that is specific to each electrode configuration using a particular voltage or current intensity. This forward-model is summarized in a matrix of values indicating field intensity achieved in different locations of the head for different energized electrode sets/pair (dimensions of the matrix is locations by electrodes). In some aspects, the electrode positions can reflect locations on the subject's heads (e.g. 100 electrodes positions around the subjects head). The forward model can then be optimized.

Once this series (e.g. 100 simulations) of models are all solved and the solutions saved as the forward model a matrix, predictions can be made as to what electrical fields will develop in the target tissue when any combination of electrodes is activates at any intensity. This is optimizing the forward model and produces the "optimized model." Moreover, optimizing the forward model according to aspects of the present invention can be done rapidly without the time consuming and costly process of developing a separate matrix or forward model for each desired intensity. Aspects of the invention use pre-solved solutions for each electrode (at one intensity per electrode) to predict what will happen if any combination of the electrodes are activated with any combination of electrode intensities (as the simple product of current intensities vector with the forward model matrix). As such, a clinician wanting to know the outcome of a specific electrode configuration (locations and intensities), can use aspects herein, to immediately predict the electric fields developed in the target tissue in response to the stimulation specified in the optimized model.

Optimization in accordance with aspects of the present invention can also allow determination of the optimal electrode configuration (electrode number, position of each electrode, current at each electrode) based on an outcome specified by the clinician, such as production of a desired electrical field at a desired tissue location. For example the clinician may want to target one part of the brain without affecting neighboring regions of the brain. Rather than the clinician trying the infinite number of combinations possible, the optimization algorithm uses the forward model solved solution series, and automatically calculates the optical electrode configuration.

In embodiments of the present invention precise forward-models of current flow, similar to that used to solve inverse problems in EEG analysis are used. The forward-models are leveraged to achieve desired electric field intensities at target brain regions while sparing other brain areas. Such electric fields are well-correlated with the desired physiological changes (i.e., neuromodulation and cortical excitation or inhibition). Using a model of the human head based on Magnetic Resonance Imagery (MRI) with different conductivities for each tissue type, the relationship between the applied current and the resulting electric field throughout the volume of the brain is numerically computed. Furthermore, this computation is carried out for specified set of electrode pairs (once for each pair of stimulating and reference electrodes), resulting in a linear system relating the distribution of the scalp current to the electric field. This puts the problem of achieving a desired intensity at the target while maintaining focality on solid mathematical footing, where linear algebraic operations and optimization techniques may be harnessed to derive optimal stimulation parameters.

The considerations on optimal stimulation are irrespective of what current-waveforms are used. For instance, sinusoidal alternating current, on/off, pulsed, or random noise stimulation are contemplated by the embodiments of the present invention. Other current wave forms may also be used.

The maximum total current delivered to the patient is a consideration. A widely accepted standard for safety and comfort of weak-current electrical stimulation (as in tDCS) is to limit the total current delivered to 2 mA. This constraint limits the effective degrees of freedom and thus the achieved intensity and focality. It will be appreciated, however, that unbounded or unconstrained conditions may be relevant to modalities other than tDCS, such as transcutaneous electrical stimulation and ECT, thus embodiments of the present invention are applicable to all noninvasive electrical stimulation modalities.

Developing the Model Image:

In an implementation of the present invention, forward model is generated using techniques similar to those described in, Jacek P. Dmochowski, Abhishek Datta, Marom Bikson, Yuzhuo Su, and Lucas C. Parra, "Optimized Multi-Electrode Stimulation Increases Focality and Intensity at Target", Journal of Neural Engineering, 8(4), August 2011, incorporated herein in its entirety. See also section below entitled "Subject specific forward model". Briefly, the method used in such an implementation uses a T1-weighted MRI image of the head and segments tissue using automated segmentation techniques implemented in freely available software packages such as FSL or SPM8. The segmentation result can then be manually corrected if desired using editing software such as Simpleware. Electrodes masks are placed on the head using an automated placing procedure which we implemented in MATLAB using standard image processing routines. Electrode placement is based on conventional and easily recognizable landmarks on the head (inion, nasion, periauricular points). The FEM mesh is then obtained using commercially or freely available meshing software (e.g. Simpleware).

An alternative prior art-method for obtaining the forward model is as follows: Obtaining a two-dimensional or 3-dimensional image of the target tissue, such as a cranial image, and ascertaining tissue properties including electrical characteristics of the tissue such as conductivities, resistivities, permittivities, capacitances, impedances, or applied energies or combinations thereof, allows for development of an "image model" of the target tissue. Image models can be developed from generic library tissue images, fluoroscopy images, MRI images, CT scans or images, other imaging modalities known in the art, or a combination of images. Tissue properties can be developed from library information, testing of the target tissue, or approximated from image data, as described in U.S. Patent Application Pub. No. US 2007/0043268 A1, incorporated herein by reference in its entirety.

A relationship of tissue resistivity to MRI gray scale that can be correlated to tissue types can be expressed by the formula:

$$R(V)=K(1-v)^E+D, \text{ where}$$

R=Resistivity;
V=Numeric value of MRI data*;
K=Multiplier value;
E=Exponent; and
D=Density value.

*The V value can be either simple MRI data values or combined values from multiple MRIs or multiple types of MRIs. Exemplary values include K=1600, E=4 and D=65.

Anisotropies/directionalities can be inferred from the anatomy or determined based on the MRI data, or a combination thereof. A direct determination is accomplished by diffusion tensor MRI (DT-MRI, or DTI). The indirect is accomplished by inferring the direction of fibers, specifically nerve fibers, by the general anatomy. DT-MRI data are sometimes called Anisotrophic MRIs.

FIG. 1 illustrates MRIs of three different types: T1, T2 and PD. Below each MRI is a gray scale. The gray scale for the T1 MRI appears to resolve three peaks which may correspond to three distinct tissue types having three different resistivities. The gray scale for T2 shows one, or possibly two, peaks, and the gray scale for PD shown one peak at a different resistivity than T2 or T1. By utilizing information from different MRI types, it is possible to enhance gray scale segmentation.

Figure 2:
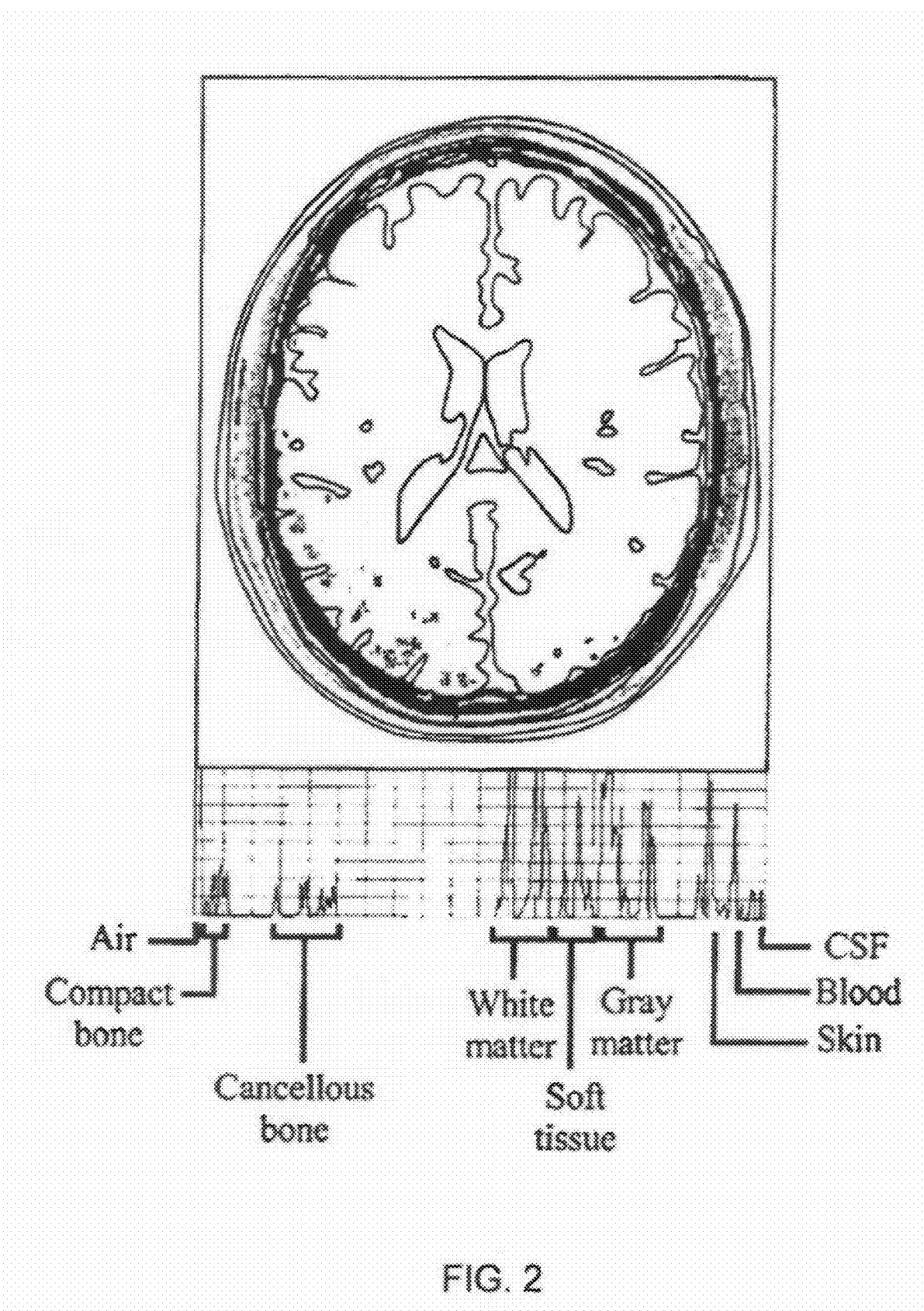
FIG. 2 is an illustration of an exemplary image of target tissue.

FIG. 2 illustrates a MRI and a plot of resistivities of tissues showing multiple resolved peaks achieved by gray scale differentiation of tissues of different resistivities. The gray scale for the MRI shown in FIG. 1 can resolve multiple peaks corresponding to various tissue types including compact bone, cancellous bone, white matter, soft tissue, gray matter, skin, blood and cerebral spinal fluid. Other resolvable tissues may include cancerous tissue, inflammatory tissue and ischemic tissue, as well as eye fluid. By having enhanced resolution of tissues, it is possible to assign more correctly the vector resistivities or other electrical values to brain or other body tissues, and thereby developing a more accurate image model.

Figure 3:
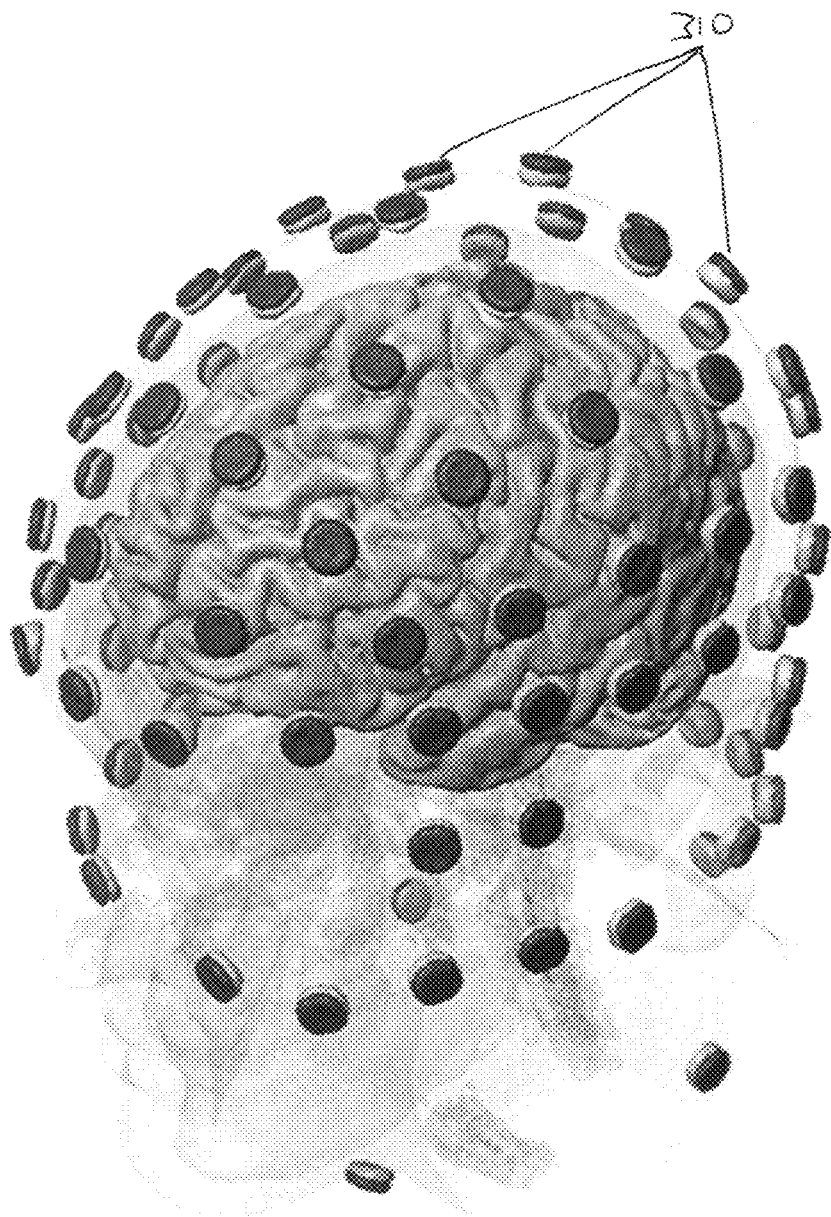
FIG. 3 illustrates an exemplary electrode configuration surrounding target tissue.
Figure 4:
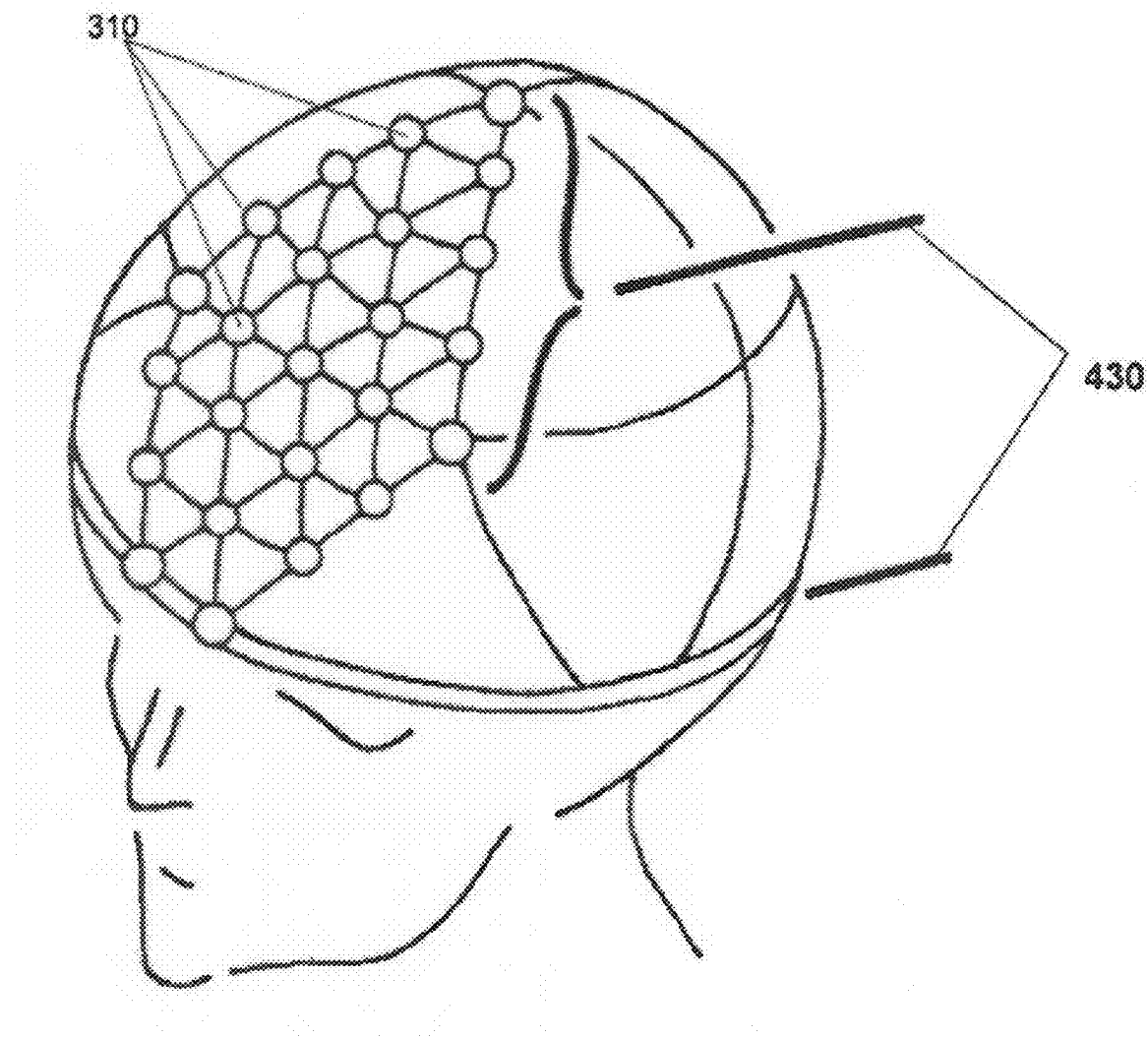
FIG. 4 illustrates an exemplary electrode configuration incorporated into a wearable device.

Electrode Configuration:

The electrode configuration is placed around the target tissue. The electrode configuration includes two or more electrodes (e.g., three or more electrodes, four or more electrodes, 8 or more electrodes, 10 or more electrodes, 100 or more electrodes, 200 or more electrodes, 256 or more electrodes). The electrodes deliver an electrical stimulation having a desired current or voltage intensity. For examples currents between about 0.1 mA and about 100 mA can be delivered to the target tissue via the electrodes in the electrode configuration. For example, voltages of between about 0.1V and about 100V can be used. Not all electrodes in the configuration need to be active. That is, in certain embodiments, some electrodes may have zero current, 0 volts while others may deliver the desired current or voltage intensity. FIG. 3 illustrates an exemplary electrode configuration around target cranial tissue, where electrodes 310 are placed around the subject's head 315. Electrodes 310 can be placed randomly or according to established systems, such as the International 10-20 system. Electrodes can be placed around the target tissue based on anatomical landmarks. Electrodes 310 can be placed on the surface of the skin, under the skin, or within the target tissue. Electrodes 310 can be incorporated into a wearable device, such as the skull cap 430 illustrated in FIG. 4.

Developing the Forward Model

Development of the forward model involves determining the electric field response in the target tissue for each electrode in the electrode configuration at a specified stimulation parameter such as current or voltage intensity. The electric field response of the target tissue can be described as the volume of tissue activated in response to the electrical stimulation.

There are different ways to determine the "volume of tissue activated". At the most basic level this includes induced brain voltage (rarely used), electric fields (same as current density), and electric field derivative (same as activating function). On a more complex level, the calculations of induced voltage/field in the brain are than passed through another set of equations that more accurately predict brain activation. These second stage filters can include 1) at the simplest a threshold (e.g. electric field greater than x is full activation, less than x is no activation); 2) the electric field may be broken down into direction where the direction themselves are based on the cortical geometry (for example the electric field perpendicular to the cortical surface) or sub-cortical anatomy (for example direction of axons); 3) the effects of electric fields on neurons may be directly computational determined (e.g. a (detailed) model so a cortical neuron). On a yet more complex level, system level and control theory analysis may be used to predict effects of cognition and behavior. Any combination of this "volume of tissue activated" solutions can form a "prior-set" of solutions wherein a set of solutions for each electrode in the electrode configuration forms the forward model.

The volume of tissue activated can be determined based on a spheres model, an individualized spheres model, and anatomical model based on gross measurements, and anatomical model based on individual images such as MRI. The above "volume of tissue activated" can be determined for a sub-set of potential stimulation configurations. Where a stimulation configuration used a set of one or more electrodes, in a specific arrangement, and a certain level of current delivered to each electrode. The number of independent configurations are tested and the "volume of tissue activated" is determined for each electrode configuration. This forms a pre-determined set of solutions. There is a time cost associated with determined the volume of tissue activated.

Finite Element Modeling (FEM) as a method for determining the volume of tissue activated can be used with the image model and the specified electrode configuration to produce the forward model. FEM techniques are described in U.S. Patent Application Pub. Nos. US 2007/0043268 A1 and US 2006/0017749 A1, both of which are incorporated herein by reference in their entirety. FEM analysis may be done using any number of commercial computer programs, such as FEMLAB by Comsol Pty. Ltd. of Burlington, Mass.

Figure 5:
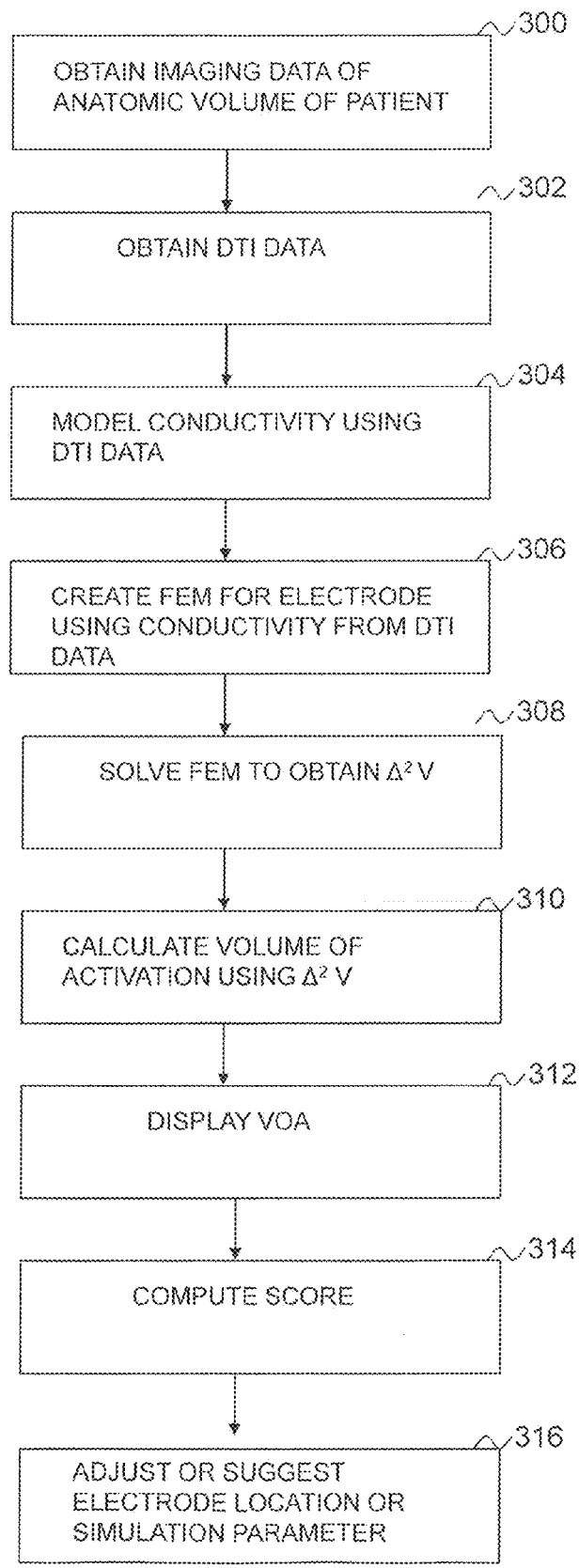
FIG. 5 illustrates a process for determining a forward FEM model of electrical stimulation of target tissue.

FIG. 5 is a flow chart illustrating generally one example of a method of using a model to calculate a volume of activation, as discussed above. Portions of the method may be embodied in any machine-accessible medium carrying instructions for executing acts included in the method. Such a method applies to deep brain stimulation (DBS) or any other electrical tissue stimulation. At 300, imaging data of an anatomic volume of a patient is obtained. In one example, this includes obtaining imaging data of a patient's brain using an imaging modality, such as computed tomography (CT) or magnetic resonance (MR) imaging modalities, for example, or another suitable imaging modality. The anatomic volume need not be all or part of the patient's brain, but could be all or part of any other anatomic structure.

At 302, in one example, diffusion tensor imaging (DTI) data is obtained (this may occur at 300, such as where a DTI MR imaging modality is used at 300). In one example, the DTI data is obtained from the same patient being analyzed. Alternatively, "atlas" or library DTI data is obtained from at least one other patient. If atlas DTI data from another patient is used, it is typically spatially scaled to correspond to the anatomic size and shape of the patient being analyzed. In one example, the atlas DTI data is based on a composite from more than one other patient. The composite atlas DTI data typically spatially scales DTI data from the different patients before combining into the composite DTI atlas. The atlas DTI data avoids the need to obtain DTI data from the particular patient being analyzed. This is useful, for example, when a non-DTI imaging modality is used at 300.

At 304, a tissue conductivity model, or image model as discussed above, is created for all or part of the anatomic volume. The tissue conductivity model is typically a non-uniform spatial distribution. Such a model more accurately represents inhomogeneous and anisotropic characteristics of the tissue anatomy. For example, the conductivity of brain tissue varies from one brain region to another. Moreover, conductivity of the nervous system is preferential to a particular direction that is also dependent on the particular location in the brain. In one example, a non-uniform tissue conductivity model is created by transforming the DTI data into conductivity data, such as by using linear transform techniques known in the art.

It should be noted that it is not required to obtain non-uniform tissue conductivity data using DTI. There exist several alternatives to using DTI based approximations for the anisotropic and inhomogeneous tissue properties for the patient specific finite element volume conductor model. One example technique would be a simple designation of a white matter and a grey matter conductivity tensor, as discussed above. These two universal conductivity tensors could then be applied to the nodes of the FEM mesh using co-registration with the anatomical MRI. In this manner, the individual voxels of the MRI data are designated as either white matter or grey matter using post-processing image analysis. Then, each such voxel is assigned a conductivity dependent on whether it was classified as white matter or grey matter, which white matter voxels having a different conductivity value than grey matter voxels. A second example technique would define individual conductivity tensors for designated brain regions (e.g., nuclei, sub-nuclei, fiber tracts, etc.). This method would allow for a more detailed representation of the tissue electrical properties than the first example technique. The conductivity tensor of each designated brain region is defined, in one example, using explicit experimental tissue impedance results and anatomical information provided by a human brain atlas. In this technique, the anatomical MRI is subdivided into different designated brain regions on a voxel-by-voxel basis using post-processing image analysis. The appropriate conductivity tensors for each designated brain region is then co-registered with the nodes of the FEM mesh.

At 306, a finite element model (FEM) is created using the conductivity data obtained at 304. In one example, the FEM model uses a default boundary condition that is appropriate for a typical electrode contact morphology. However, in another example, the FEM model includes an electrode-specific boundary condition that is tailored to the morphology of a particular electrode contact or contacts to be used in the DBS or other procedure. The FEM model provides for non-uniform conductivity in the tissue, such as by using a DTI-derived other conductivity value at each node in the FEM mesh. The FEM model may include aspects that are not obtained from the DTI-derived data. In one such example, the FEM mesh models a thin encapsulation sheath about the electrode lead body, as discussed above, which is not derived from the DTI data.

At 308, in one example, the FEM is solved for the electric potential distribution or the second difference ($.DELTA^2 V$) of the electric potential distribution, such as by using FEM solver software. In one example, the FEM is solved for a normalized stimulation amplitude of 1V or 0.1 mA. In another example, for a different electric stimulation amplitude, the resulting electric potential distribution (or second difference of the electric potential distribution) is multiplied by a scale ratio of the different electric stimulation amplitude to the normalized electric stimulation amplitude.

Scoring of Solutions Based on VOA

In one embodiment as outlined below, solutions are optimized to reduce the error between a desired electric field distribution and the electric field distribution achieved by applying the optimized current to electrodes. In other embodiments additional steps are taken to SCORE solutions based on additional analysis including volume of activation (VOA). Scoring may be integrated into the optimization process as described below, or used as an additional processing, data display, and user interface step. The prior art solved and scored each electrode configuration and current individually and iteratively without optimization at tremendous computational and time cost.

At 310, a volume of tissue activation (VOA) or other volume of influence is calculated, in one example, using the second difference of the electric potential distribution. The VOA represents the region in which any neurons therein are expected to typically be activated, that is, they are expected to generate propagating action potentials at the stimulus frequency in response to the electrical stimulation delivered at the stimulation electrode contact. Conversely, neurons outside the VOA are expected to typically remain unactivated in response to the electrical stimulation. Neurons in the volume of influence are expected to be modulated (neuromodulation) in a manner related to the strength of regional electric field or some function there-of. In one example, a particular threshold value of the second difference of the electric potential distribution defines the boundary surface of the VOA.

As discussed above, the particular threshold value defining the boundary of the VOA is determined as follows. First, model neuronal elements are positioned relative to the electrode using known neuroanatomical information about specific fiber pathways and nuclei of interest near the electrode. These generalized positions of the model neuronal elements are then refined, such as by using explicit "patient-specific" information provided in the DTI or anatomical MR imaging data. For example, the DTI imaging data describes the inhomogeneous and anisotropic tissue properties near the electrode. In this example, such DTI imaging data is used to explicitly define one or more axonal trajectories, if needed, or to help define nuclear boundaries specified in the anatomical MRI.

A model of these neurons is then created. In one example, the neurons are modeled using an axon model, which is a simplified form of a neuron model. An example of an axon model is described in Cameron C. McIntyre et al., "Modeling the Excitability of Mammalian Nerve Fibers: Influence of Afterpotentials on the Recovery Cycle," J. Neurophysiology, Vol. 87, February 2002, pp. 995-1006, which is incorporated by reference herein in its entirety, including its disclosure of axon models. In another example, a more generalized neuronal model is used, an example of which is described in Cameron C. McIntyre et al., "Cellular Effects of Deep Brain Stimulation: Model-Based Analysis of Activation and Inhibition," J. Neurophysiology, Vol. 91, April 2004, pp. 1457-1469, which is incorporated by reference herein in its entirety, including its disclosure of neuronal models. The neuron model describes how the neurons will respond to an applied electric field, that is, whether the neuron will fire and whether the neurons will generate a propagating action potential.

In one example, using this neuron model to simulate how the neurons (located as determined from the DTI-derived conductivity data, in one example) behave, the threshold value of the second difference of electric field that will result in such propagating action potentials is calculated. The stimulating influence of the electric field is applied to the model neurons to define a threshold value. This threshold value is then used to define the boundary of the VOA in the non-uniform conductivity tissue, as discussed above.

It should be noted that calculation of explicit threshold criteria for each patient is not required. For example, in a more generalized situation, threshold criteria will have already been determined using the detailed neuron models under a wide variety of different stimulation conditions. Once these threshold criteria have been determined, they need not be re-determined for each subsequent patient.

It should also be noted that using a threshold criteria upon the second difference of the potential distribution in the tissue medium is a simplified technique for quickly determining a VOA or other volume of influence. The intermediate step of using the second difference of the potential distribution is not required. In an alternate example, the FEM model is directly coupled to a detailed neuron model, such as a multi-compartment neuron model that is oriented and positioned in the FEM model to represent at least one actual nerve pathway in the anatomic volume.

At 312, the calculated VOA region is displayed, such as on a computer monitor. In one example, the VOA is displayed superimposed on the displayed imaging data or a volumetric representation derived from such imaging data. In another example, an anatomic boundary or other representation of an anatomic structure is superimposed on the VOA and imaging data or the like. The anatomic boundary data is typically obtained from an atlas of brain anatomy data, which can be scaled for the particular patient, as discussed above. Alternatively, the anatomic representation is extracted from the imaging data for the patient being analyzed. In one example, the anatomic representation is a line depicting one or more boundaries between particular nucleus structures or other regions of the brain, such as the STN, IC, or ZI illustrated above in FIG. 1B.

In any case, by viewing a representation emphasizing one or more brain regions displayed together with the VOA, the user can then determine whether a particular anatomic region falls within or outside of the modeled VOA. The user may want a particular anatomic region to be affected by the DBS, in which case that region should fall within the modeled VOA. Alternatively, the user may want a particular region to be unaffected by the DBS, such as to avoid certain unwanted DBS stimulation side effects, as discussed above. This evaluation of whether the VOA is properly located can alternatively be performed by, or assisted by, a computer algorithm.

For example, the computer algorithm can evaluate various VOA's against either or both of the following input criteria: (a) one or more regions in which activation is desired; or (b) one or more regions in which activation should be avoided. In one example, at 314, the computer algorithm creates a score of how such candidate VOAs map against desired and undesired regions. In one example, the score is computed by counting how many VOA voxels map to the one or more regions in which activation is desired, then counting how many VOA voxels map to the one or more regions in which activation is undesired, and subtracting the second quantity from the first to yield the score. In another example, these two quantities may be weighted differently such as, for example, when avoiding activation of certain regions is more important than obtaining activation of other regions (or vice-versa). In yet another example, these two quantities may be used as separate scores.

At 316, the score can be displayed to the user to help the user select a particular VOA (represented by a particular electrode location and parameter settings). Alternatively, the algorithm can also automatically select the target electrode location and parameter settings that provide the best score for the given input criteria.

In one example, the VOA is displayed on a computer display monitor of an image-guided surgical (IGS) workstation, such as the StealthStation® from the Surgical Navigation Technologies, Inc. (SNT) subsidiary of Medtronic, Inc., for example. The VOA can be displayed on the IGS workstation monitor with at least one of the imaging data representing the anatomic volume, the target electrode location, a burr hole or other anatomic entry point, a trajectory between the anatomic entry point and the target electrode location, or an actual electrode location.

In one IGS workstation example, the displayed VOA corresponds to a target electrode location.

After the electrode is positioned at the target location, there remains the challenging task of adjusting the DBS stimulation parameters (e.g., the particular electrode contact(s) of a plurality of electrode contacts disposed on the same DBS leadwire, pulse amplitude, pulsewidth, electrode "polarity" (i.e., monopolar or bipolar electrode return path), electrode pulse polarity (i.e., positive or negative), frequency, etc.). In one example, the IGS workstation or a DBS pulse generator programmer includes the above-described VOA methods to assist the user in selecting an appropriate combination of DBS stimulation parameters, such as by using the scoring techniques discussed above. In essence, for each electrode position, a forward model can be calculated. As discussed above, this is time consuming and costly.

Figure 6:
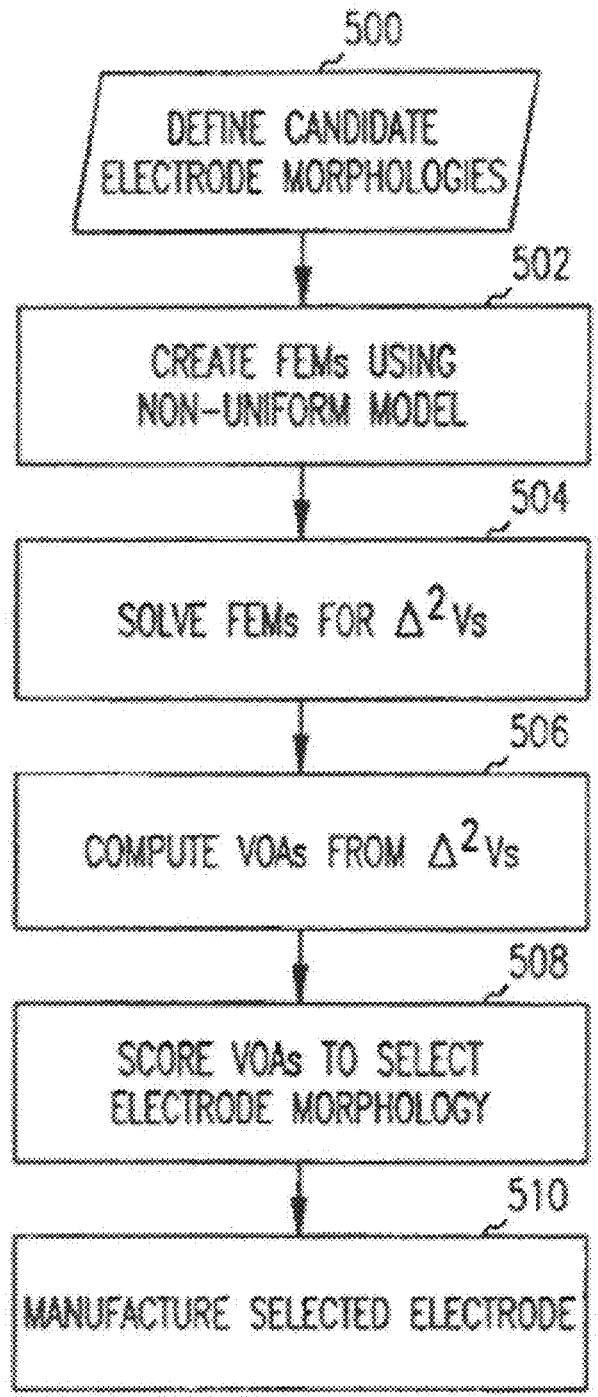
FIG. 6 illustrates a process for determining an optimized model of electrical stimulation of target tissue according to the present invention.

FIG. 6 is a flow chart illustrating generally one example of a method of using an FEM model to calculate a volume of activation, as discussed above, and using the volume of tissue activation to select a particular electrode configuration. Portions of the method may be embodied in any machine-accessible medium carrying instructions for executing acts included in the method. Such a method applies to selecting an electrode configuration for deep brain stimulation (DBS) or for any other electrical tissue stimulation. At 500, a set of N candidate electrodes are defined, where N is an integer greater than 1. Defining the candidate electrode configurations typically includes providing information about the size, shape, or arrangement of electrode contacts on a leadwire. Such information is typically in a form in which it can be used as input to a finite element model (FEM). At 502, a FEM is created for each candidate electrode position. The FEMs typically use non-uniform conductivity model of a desired region of interest. At 504, each FEM is solved for a second difference in the electric potential distribution. At 506, a volume of activation (VOA) is computed for each candidate electrode morphology from its corresponding second difference in the electric potential distribution. The boundary of the VOA is typically obtained from a threshold value that is based on a neuron or axon model, as discussed above. At 508, the VOAs are scored, as discussed above, or otherwise evaluated to select one or more electrode locations that exhibit a desired VOA, or a VOA that is deemed more desirable than the VOA of one or more other electrode morphologies. At 510, at least one electrode is manufactured using the selected at least one electrode morphology.

Optimizing the Forward Model:

The above image collection and modeling techniques require time intensive and costly computations to determine the volume of tissue activated for a particular electrode configuration using specific stimulation parameters. Moreover, changes to electrode positions and or changes to stimulation parameters, such as current or voltage intensities, require recomputation to verify the new volume of tissue activated. For example, to solve and score a multitude of solution as described above is very costly computationally and may not result in an optimal configuration.

It has been found that changes to the forward model, and particularly changes to current or voltage intensities can be optimized or predicted using linear approximations. This avoids the need for re-running costly computational forward models and greatly enhances the speed to which electrical stimulation procedures can be modeled, outcomes predicted, and treatments prescribed.

In an aspect, the governing equation for the optimization process is given by the simple linear relationship:

$$E = MI \quad (1)$$

where:

E is a vector that represents the field magnitudes at multiple locations in the tissue.

I is a vector that represents the currents at multiple electrodes.

M is a matrix that linearly relates the currents I to the fields E and is called a "forward model".

The goal of optimization is to choose an optimal current vector I* with a net-zero current such that desired field magnitudes E* are achieved, while maintaining maximum current limits:

$$I^* = \operatorname*{argmin}_{I} \|E^* - MI\|^2 \text{ subject to constraint } |I| < I_{max} \quad (2)$$

and sum $(I) = 0$

Other constraints such as "minimum number of non-zero currents", "maximum allowable field intensities" or "maximum allowable current densities" can be incorporated into this approach using additional optimization criteria (such as an L1-norm penalty term) or linear boundary constraints.

The forward model M can be computed from a 3D distribution of electrical conductances and the locations of the electrodes and locations for which the field is to be computed. The values in matrix M are the solution to the quasi-static Laplace equation (simplification of Maxwell equations) under Dirichlet boundary conditions which govern the relationship between static currents I, ie. the boundary conditions, and the resulting electric fields E, i.e. the solutions, in a purely resistive material. Each column in matrix M represents the solutions for a unit current in a given electrode pair (all other electrode carrying no current). Each row in matrix M represents a different location in the tissue. If N electrodes are used and a single electrode is used as a common reference for all pairs, then matrix M has N−1 columns. The number of rows of matrix M scales with the number of 3D locations in the tissue for which one would like to specify field magnitudes. To be more specific, there is one such matrix for each field orientation: $M_x$ for lateral-direction field $E_x$, $M_y$ for depth-direction field $E_y$, and $M_z$ for vertical-direction field $E_z$:
$M=[M_x^T, M_y^T, M_y^T]^T$, and $E=[E_x^T E_y^T E_y^T]^T$. Thus the number of rows is precisely 3 times the number of tissue locations of interest.

The 3D current distribution can be obtained, for instance, from a segmentation of a 3D image of the tissue such as MRI, CT, DTI, etc. Such a segmentation can be reformulated in a finite-element model (FEM), which is then used to provide an efficient numerical solution to the Laplace equation. Commercial software such as Abacus or Comsole is available to perform these numerical FEM computation.

In an example, the optimization problem given in equation (2) can be formulated on the basis of the linear relationship (1) and that matrix M does not have to be recomputed using computationally intensive numerical approaches for every possible choice of I. Thus the optimization can be solved strictly using efficient least-squares optimization procedures and do not require an expensive trial-and-error search for I.

Examples of optimization methods consistent with embodiments of the present invention are set forth in Dmochowski, Datta, Bikson, Su and Parra; "*Optimized Multi-Electrode Stimulation Increases Focality and Intensity at Target*," Department of Biomedical Engineering, City College of New York,—City University of New York, incorporated herein in its entirety. These optimization schemes or methods include the following algorithms, including: Least Squares (LS); Weighted Least Squares (WLS) with individual constraint; and Linear Constrained Minimal Variance (LCMV), and Lease Absolute Shrinkage and Selection Operator LASSO. Other algorithmic methods may be used as optimization schemes for optimizing non-invasive electrical stimulation modalities.

Figure 7:
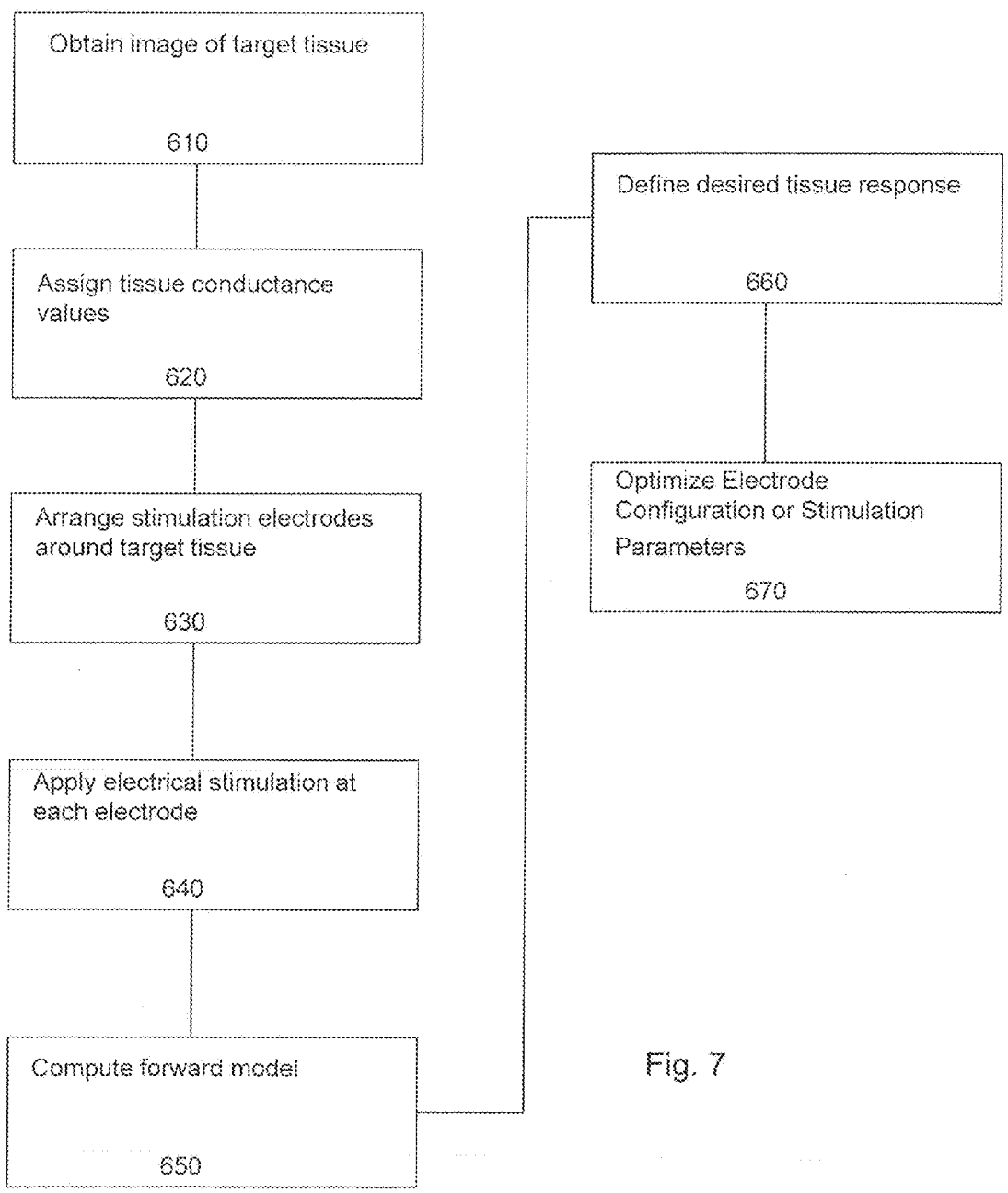
FIG. 7 illustrates a process for determining an optimized model of electrical stimulation of target tissue according to the present invention.

FIG. 7 is a flow chart illustrating generally one example of optimizing a model to determine or predict changes to a stimulation procedure, as discussed above. Portions of the method may be embodied in any machine accessible medium carrying instructions for executing acts included in the method. Such a method applies to electrical stimulation of bodily tissue, including transcranial tissue. At 610, an image of target tissue is obtained, as discussed above. The image can be obtained from generic library tissue images, PET images, MRI images, CT scans or images, or a combination of images. The target tissue can be any bodily tissue including transcranial tissue.

At 620 conductance values are determined for the target tissue. Conductance values can be a uniform or a non-uniform spatial distribution. Conductance values can be determined from pre-existing data of generic tissue images, target tissue specific data derived from testing, or determined from grey scale MRI images of the target data as described above.

At 630, electrodes are configured about the target tissue. For example, electrodes are distributed around a patient's head according to the International 10-20 System. The number of electrodes can range from 2 or more, 3 or more, 10 or more, 100 or more 200 or more, and 256 or more. A current and voltage intensity is determined. The applied current can be in the range of about 0.1 mA to about 100 mA. The voltage can be in the range of about 1V to about 100V. In aspects, the same current or voltage intensity is used for each electrode in the electrode configuration.

At 640, electrical stimulation is applied to each electrode, using the same current and voltage intensity. For each electrode stimulation, the volume of tissue activated is calculated. Cataloguing each volume of tissue activated for each electrode stimulation results in the development of the forward model at 650.

At 660 a desired tissue response is defined. For example, a particular volume of tissue activated may be desired. Other examples include maximizing one are of tissue activation while minimizing other areas of tissue activation. A particular physiological response may be desired.

At 670, the forward model is optimized, as described above, to predict the electrode configuration and current or voltage intensities required to produce the desired tissue response.

Figure 8:
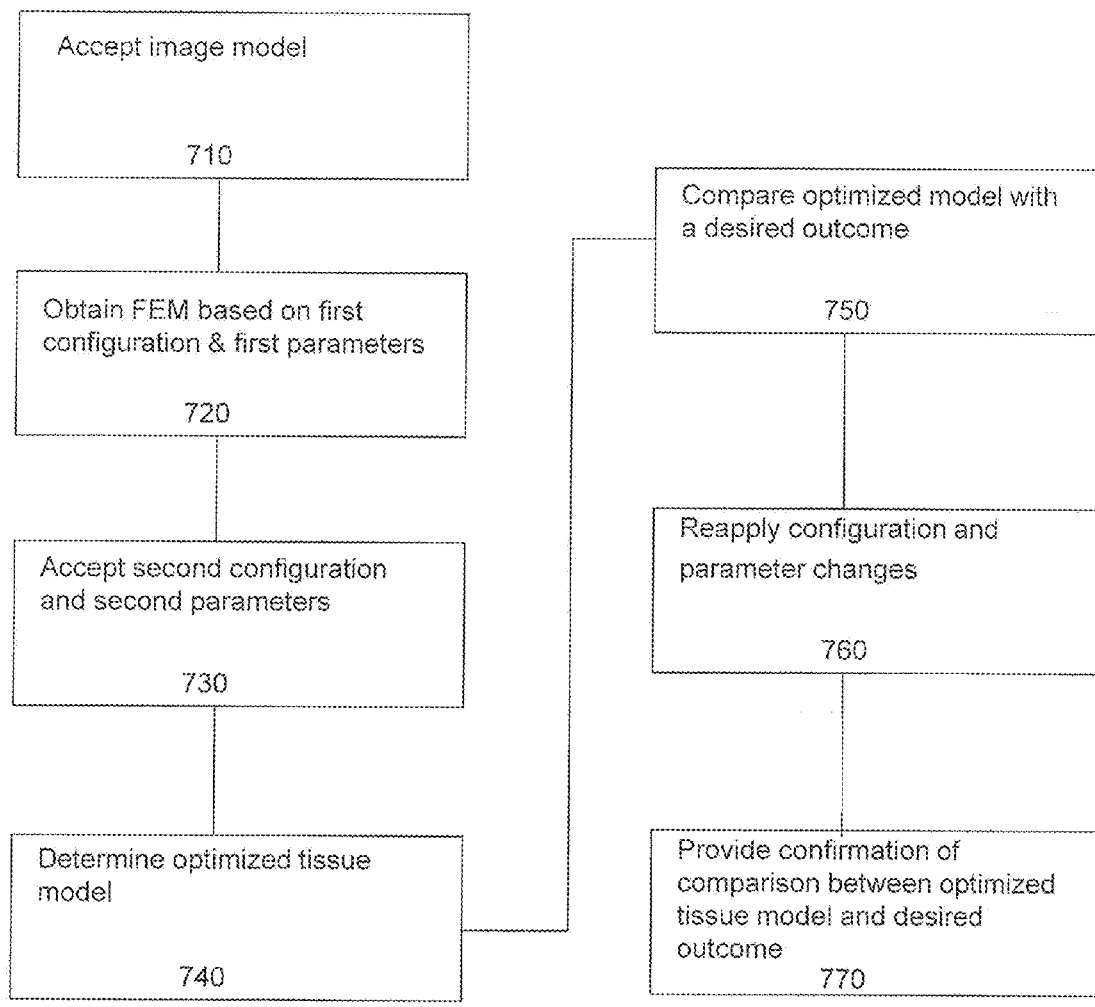
FIG. 8 illustrates a flow chart of an implementation of the present invention.

FIG. 8 is a flow chart illustrating generally one example of optimizing a model to determine or predict changes to a stimulation procedure, as discussed above. Portions of the method may be embodied in any machine accessible medium carrying instructions for executing acts included in the method. Such a method applies to electrical stimulation of bodily tissue, including transcranial tissue.

At 710, an image model, as described above is accepted. The image model includes a 2-D or 3-D image of the target tissue along with certain electrical characteristics of the target tissue. For example, the image model can be of transcranial tissue and can include tissue conductance values. It will be noted that the image model need not be developed locally but can be down loaded from a file. The image model can be generic image model or a patient specific image model.

At 720 Finite Element Model (FEM) of the image model is obtained. The FEM is based on a particular electrode configuration, such as electrodes arranged according to the International 10-20 System. The number of electrodes can range from 2 or more, 3 or more, 10 or more, 100 or more 200 or more, and 256 or more. The FEM is also based on a particular stimulation parameter (e.g., current and voltage intensities). A current and voltage intensity is determined. The applied current can be in the range of about 0.1 mA to about 100 mA.

The voltage can be in the range of about 1V to about 100V. In aspects, the same current or voltage intensity is used for each electrode in the electrode configuration. It will be noted that the FEM does not need to be developed locally but can be downloaded from a file.

At 730 a second electrode configuration (e.g., movement of one or more electrodes in the first electrode configuration) and/or a second stimulation parameter (e.g., a change in the current or voltage intensity from the first stimulation parameter) is accepted.

At 740 the FEM is optimized using the optimization formula described above to determine the tissue response from the changes in electrode configuration or stimulation parameters. In an example, a desired tissue response is determined and the electrode configuration and stimulation parameter predicted utilizing the optimization formula described above. At 750 the optimized model can be compared with a desired outcome or physiological response. In an example, the optimized model can be compared against certain constraints, such as maximum voltages or currents at one electrode or all electrodes, or maximum electrical fields at any tissue location.

At 760, the electrode configuration and stimulation parameters can be adjusted based on the optimized model and the desired outcome or known constraints. The desired outcome can be adjusted based on the electrode configuration and stimulation parameters used to optimize the model.

At 770, confirmation of the optimized model and the desired outcome, along with the electrode configurations and stimulation parameters can be provided to a user via a user interface, a print-out or other means known in the art.

Additional Embodiments

Aspects of the present invention use a matrix set of solutions to determine the "volume of tissue activated" or "region of influence" for a separated electrode configuration (one in which the volume of tissue activated has not been determined)—this is a new electrode configuration of interest. This is done by combining the set of solutions in a manner that minimizes error. The solutions may, for example, be each weighted linearly such that there is a weight associated with each solution, and the each solution multiplied by this weight added. For example, a series of solutions of electric fields in the brain. The weight may be determined such that the electrical current injection by the summation of each solution multiplied by its respective weight equals the electrical current injection by the new electrode configuration of interest. The weight may be determined by minimizing the error between the combined electrical current injected by the set of solution multiplied by the weights and the electrical current injection by the configuration of interest. The weight may be determined by other means including random selection and testing or based in a linear summation or prior knowledge about the electrode configurations. The time cost of determining these weights, and then by multiple each prior solution bits respective weights, and then addition of this new multiplied set of solutions, is less than the time cost of running a forward model (e.g., a finite element model) of the new configuration. The computational cost of determining these weights, then multiplying each prior solution by its respective weights, and then addition of this new multiplied set of solutions, is less than the computational cost of running a forward model of the new configuration. The complexity cost of determining these weights, then multiplying each prior solution bits respective weights, and then addition of this new multiplied set of solutions, is less than the complexity cost of running a forward model of the new configuration.

In another aspect, the weights applied to each prior-solution of volume of tissue activation are determined by an optimization algorithm. The optimization algorithm determines the optimal weight that may be applied to the prior-set of solutions to achieve a desired outcome. The optimization algorithm achieves this at a time and computational cost that is less than trying every possible electrode configuration. The optimization algorithm compares the set of prior solutions (e.g., prior volume of tissue activation) with the solution corresponding to the desired clinical outcome (e.g., new volume of tissue activation) and then determines the weight necessary to make these as "close as possible." The criteria for "as close as possible" are determined by pre-set conditions of the operator and can include minimizing the difference between the clinically desired "volume of tissue activation" and the volume of tissue activation by a configuration determined by the algorithm.

In one implementation the following steps are taken: The electric fields generated (forward model FEM) from monopole stimulation with a single electrode with 1 mA (or 1V) is calculated using a head model. This prior-solution is done for 128 electrode positions. The return electrode is at a fixed position for all electrode stimulations. This results in a set of 128 prior-solutions of electric fields in the head. This can be done "off-line" with a higher time and computational cost. The user interface allows a clinician to select to activate any combination of these 128 electrodes with any level of current (or voltage) at the same time. This is done by the clinician indicating how much current X to apply at each of the 128 electrodes. The position of each of these electrodes corresponds to the position of electrodes in the prior-solution. The current at each electrode does not have to be the same and can be zero. (On-line) the electric field generated by the clinician selected configuration is determined as follows:

For each electrode selected by the clinician a level of current X is specified. The prior solution (for 1 mA or 1 V) associated with each electrode is multiplied by X. This new set of solutions is then added together. The time and computational cost associated with this operation is minimized. The results of this operation are displayed to the clinicians. The results of this operation can determine the conditions of stimulation.

In another implementation the following steps are taken: The electric fields are generated (forward head model FEM) from monopole stimulation with a single electrode with 1 mA (or 1V) and calculated using a head model. This prior-solution is done for 128 electrode positions. The return electrode is at a fixed position for all electrode stimulations. This results in a set of 128 prior-solutions of electric fields in the head. This can be done "off-line" with a higher time and computational cost. The user interface allows a clinician to select a desired electric field distribution in the head. How much current to apply to each electrode to achieve this desired electric field distribution in the head is then calculated. This is done by comparing the set of prior-solutions with the desired electric field distribution and then determining how much current to apply to each electrode to minimize the difference between the desired electric field distribution and the electric field distribution induced by applied said current to the electrodes. The results of this operation are displayed to the clinicians. The results of this operation can determine the conditions of stimulation.

In another example, software calculates the stimulation efficacy and target specificity for a given stimulation protocol. This software includes a 3-D representation of the head impedance including the scalp, skull, CSF, and brain compartments. The 3-D representation requires manually-assisted segmentation of anatomical MRI scans. The user (clinician) can place two or more electrodes on the segmented scalp surface and simulate brain modulation and iteratively "explore" high density transcranial electrostimulation configurations. In prior-art applications, for each configuration change, the predicted brain modulation must be "re-solved", which takes time. In addition, placing the electrodes and determination of the current flows has been an ad-hock process. The optimal configuration may ultimately depend on an integration of patient, disease, and clinical experience related factors, and it is thus useful for a clinician to be able to intuitively and rapidly evaluate a range of configurations.

The high spatial specificity provided by in aspects of the present invention offers the opportunity to design a stimulation protocol that is tailored to the individual subject and the desired target location. Specifically, the task for the targeting methodologies disclosed herein is to determine the ideal electrode locations and to compute the required current flows through each of these electrodes; moreover the targeting processes should be accessible to a clinician using a PC, desktop computer, or portable computing device. Three technical challenges associated with the targeting processes disclosed herein include: (1) Automatic patient specific MRI segmentation; (2) Acceleration of the computational time for predicting brain modulation in response to a given stimulation configuration (3) Computation of the optimal electrode locations and currents for a user selected brain target.

Forward Model

High resolution (gyri/sulci precise) MRI derived finite element (FE) human head models were generated by segmenting grey matter, white matter, CSF, skull, muscle, fatty tissue, eyes, blood vessels, scalp etc. Each model ay comprise >10 million elements with >15 million degrees of freedom. The induced cortical electric field/current density values are calculated and used to predict regions of brain modulation.

Subject Specific

To obtain a subject specific prediction of current flows existing software packages were used to automatically segment a given subject's anatomical MRI. As significant effort by the research community has already generated a number of publicly available segmentation packages that focus on MRI segmentation (Shattuck & Leahy, 2002, Dogdas 2005, see brainsuite.usc.edu). These are adapted to integrate with the commercial FEM solver such as SIMPLEWARE (SIMPLEWARE LTD. to import MRI scans, segmentation, creating FE mesh, and COMSOL INC. for FEM computation). The result of this integration work was a software package that takes an anatomical MRI and computes the required forward models for each electrode location.

Variability in anatomy is well characterized by head size, gender, and age. Therefore, a set of standard forward models can be computed and provided as part of the real-time clinician interface to cover a range of subjects to be selected according to these criteria. If a subject-specific MRI is available the corresponding forward-model can be computed remotely using high-end computers.

In another example, computationally costly segmentation and FEM solving is run on a patient specific basis, while physician targeting software can operate on real-time by virtue of using pre-solved FEM solutions.

Another example relates to real-time optimization of stimulation protocols. It has been found that current flows within the brain are a linear superposition of the currents generated by each electrode. Based on this observation the optimization problem can be formulated as a constrained least-squares problem. Least squares aims to minimize the square difference of a desired current distribution (specified by the clinician) with the achievable current distribution as predicted by the FEM. The method is computationally efficient as the predicted current distribution can be formulated as a linear combination of the "forward model" that has been previously computed for each electrode. The forward model computation using the FEM is computationally expensive and can be performed remotely (along with segmentation).

Standard electrode locations to facilitate proper electrode placement (10/20 system conventionally used in EEG). While this is not typically required, one can increase specificity by confirming electrode locations with conventional 3D electrode-localization hardware (e.g. Fastrak, Patriot, see cortechsolutions.com). The constraints in the optimization procedure implement the requirements that currents at each electrode do not exceed some threshold value (corresponding to skin irritation and perception limits) as well as limits on maximum current flows within the tissue (safety limits). Analogous optimization problems are adapted with sensor arrays in acoustics (Parra, 2006). The computationally expensive step of computing the FEM is performed in advance for a set of standard electrode locations (, while the optimization of the electrode currents to target a specific cortical area is performed in real-time. A GUI allows the physician to define the target location and inspect the expected optimal current distribution.

Targeting Software

In another example, targeting software calculates the stimulation efficacy and target specificity for a given stimulation protocol. This software includes a 3-D representation of the head impedance including the all significant anatomical compartments. In the system the 3-D representation requires manually-assisted segmentation of anatomical MRI scans. The user (experimenter) can place two or more electrodes on the segmented scalp surface and predict resulting current distributions on the brain. In the current system, for each configuration change, the predicted current distribution in the brain must be recomputed, which takes time. In addition, placing the electrodes and deciding on the adequacy of resulting current flows is currently an ad-hoc process. The optimal configuration may ultimately depend on an integration of various factors, including patient brain anatomy, desired target area, safety and efficacy considerations. This software allows the experimenter to intuitively and rapidly evaluate a range of electrode configurations.

The high spatial specificity provided by HD-TES offers the opportunity to design a stimulation protocol that is tailored to the individual subject and the desired target location. Specifically, the task for the HD-TES targeting software is to determine the ideal electrode locations and to compute the required current flows through each of these electrodes; moreover the targeting software should be accessible to an experimenter using a conventional PC. There are three technical challenges related to this task: (1) Automatic patient specific MRI segmentation; (2) Acceleration of the computational time for predicting brain modulation in response to a given stimulation configuration (3) Computation of the optimal electrode locations and currents for a user selected brain target. These challenges can be addressed with two software modules, one for computing the head model of the current flows based on anatomical MRI, and the second for optimizing the applied currents and electrode locations.

Subject Specific Forward Model.

To obtain a subject specific prediction of current flows, existing software packages can be used to automatically segment a given subject's anatomical MRI. As significant effort by the research community has already generated a number of publicly available segmentation packages that focus on MRI segmentation (Shattuck & Leahy, 2002, Dogdas 2005, see brainsuite.usc.edu). These packages can be adapted to integrate with a commercial FEM solver (e.g., SIMPLEWARE LTD. to import MRI scans, segmentation, creating FE mesh, and COMSOL INC. for FEM computation). The result of this integration work is a software package that takes an anatomical MRI and computes the required forward models for each electrode location. Fully automated segmentation is a challenging problem in the art. As such, the accuracy of automated tools are compared to a hand-segmented MRI and evaluated to see if the differences in automated vs. hand-segmentation leads to significantly different predicted cortical current distributions.

Variability in anatomy is well characterized by head size, gender, and age. Therefore, a set of standard forward models will be generated and provided as part of the real-time targeting module.

In an example, the computationally expensive step of computing the FEM is performed in advance for a set of standard electrode locations, while the optimization of the electrode currents to target a specific cortical area is performed in real-time. The GUI allows the experimenter to define the target location and inspect the expected optimal current distribution in real-time.

EXAMPLES

Figure 9:
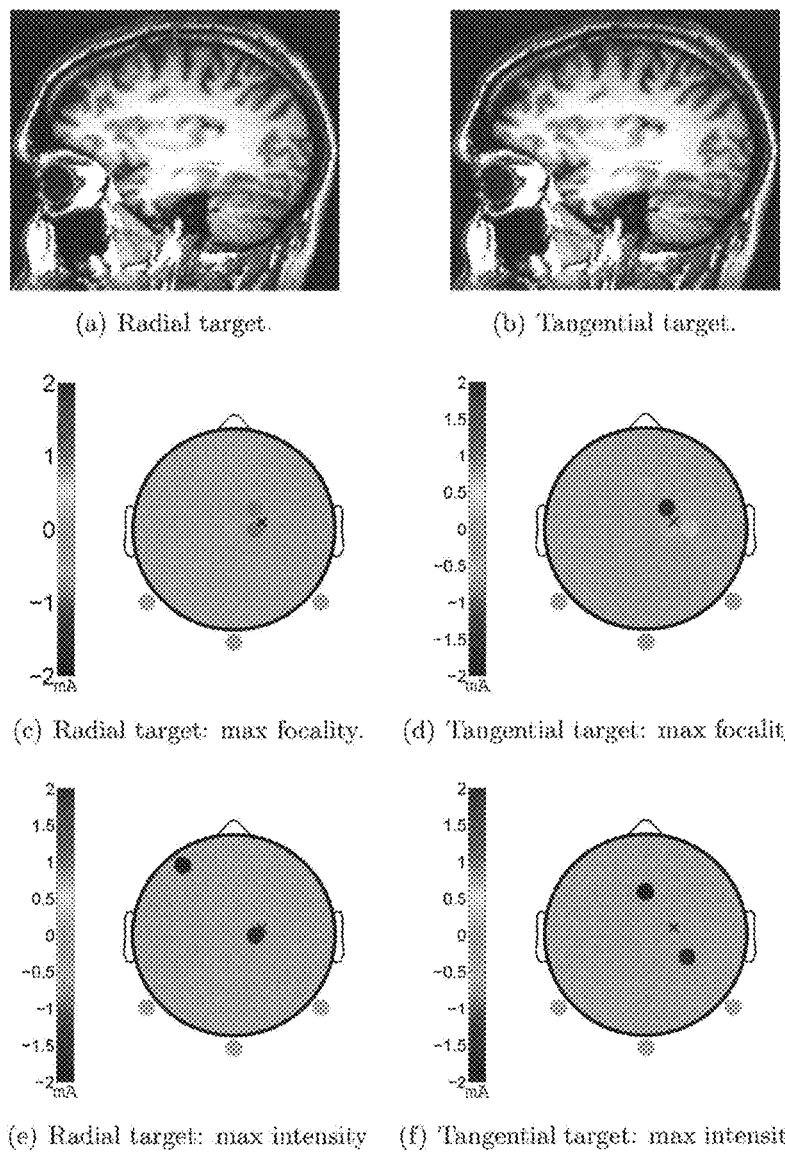
FIG. 9a illustrates a radial target of selected tissue.
FIG. 9b illustrates a tangential target of selected tissue
FIGS. 9c-f illustrate optimal current distribution as a function of desired orientation and criterion.

It has been found that the optimal solution of electrode location and current density varies non-trivially with the desired orientation and criterion. To illustrate the strong dependence of the optimal currents on the desired orientation, we select a target located on a gyms on the posterior side of the central sulcus, and then compute the optimal solutions in both radial and tangential directions, as shown in FIGS. 9a and 9b.

Figure 10:
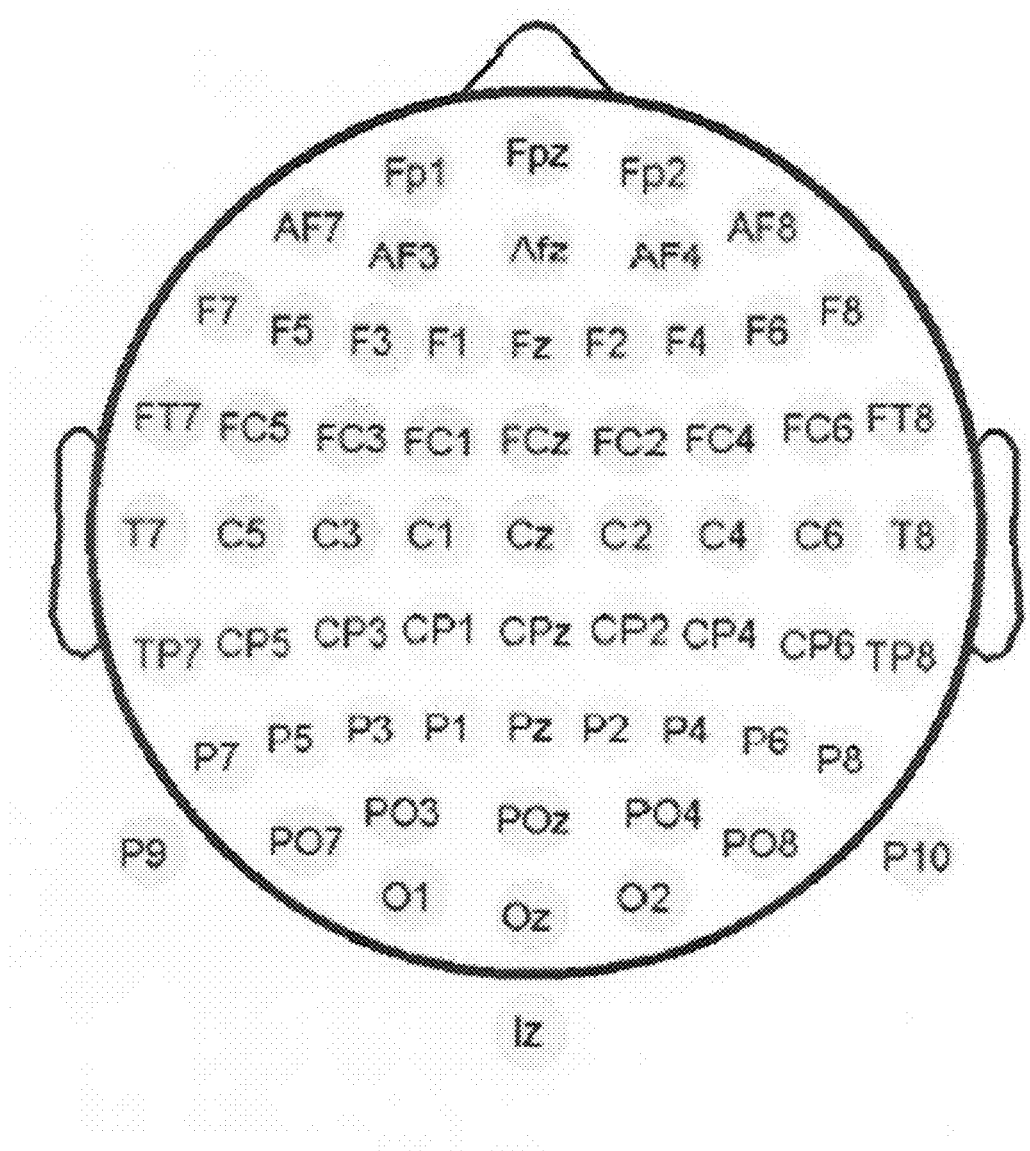
FIG. 10 illustrates a two dimensional visualization of the standard 10/10 electrode arrangement.

Both focality and intensity are optimized yielding four total solutions, illustrated in FIGS. 9c-f. The current distributions are displayed using a modified version of the EEGLABS topoplot function which renders the applied scalp currents in (EEG analysis, the values typically represent recorded electric potentials) in two dimensions using the conventional schematic for the 10/10 international system. Each electrode is represented with a circle and grey scale shading indicating the amount of current injected into that electrode (in units of mA). The electrode placement is consistent with the electrode placement of FIG. 10, which illustrates the 10/10 international system for electrode placement. It will be appreciated that any standard electrode placement system can be used, including the 10/10 system, the 10/20 system, the concentric system or the geodesic system.

The disparity between the optimal currents for the various orientations/criteria is apparent from the schematics of FIGS. 9c-f. In the radial case, the maximally focal solution takes the form of a positive two-electrode "pad" over the target, with six surrounding electrodes employed for the return currents. This configuration may be thought of as an "elongated 4×1." On the other hand, when desiring tangential current flow, the optimal currents are defined by a two-electrode anode, with a strong one-electrode, in addition to weaker components adjacent to the anode and cathode. The close proximity of the major stimulating and return electrodes should be noted. This is in stark contrast to the maximally intense solutions of FIGS. 9e and 9f, which take the form of a semi-distant bipolar configuration. It should be noted that maximum target intensity does not arise by spacing the electrodes maximally apart, as intuition may suggest. Indeed, the optimal placement of the two electrodes is dependent on the desired field orientation at the target: in the radial case, the anode is placed directly over the target. And in the tangential case, the target lies between the anode and the cathode.

Referring to FIG. 11, the coronal, sagittal and axial slices of the resulting electric field intensity and orientation are illustrated. These slices intersect the target location. The half-max radii of the focality optimized radial and tangential schemes are 44 mm and 46 mm, respectively (each with a target intensity of 0.1 V/m as specified by the hard constraint). Note that that the maximum electric field occurs at a region nearby, but not precisely at, the target. This is in part a drawback of LCMV, but mostly stems from limitations imposed by the laws of volume conduction and encapsulated by the properties of the forward-model matrix. The maximum intensities yielded for the radial and tangential targets are 0.3 V/m and 0.35 V/m; in general we have observed that larger optimized target intensities are attainable with tangential stimulation. The results are summarized in FIG. 12, which also displays F(r) for the radial case when optimized for focality with the half-max radius indicated.

In a further example, WLS attained a greater focality than LCMV at the expense of misaligned field direction at the target. A comparison of the $l_1$ norm constrained LCMV and WLS schemes in terms of the intensity-focality trade-off for two targets was made. The two targets were a gyms anterior of the central sulcus with radial field direction specified (see FIG. 13a) and the anterior side of the central sulcus having a specified tangential current flow (see FIG. 13b). Orientations were selected perpendicular to the cortical sheet as polarization of pyramidal cell somata is maximal with such orientation.

Figure 13:
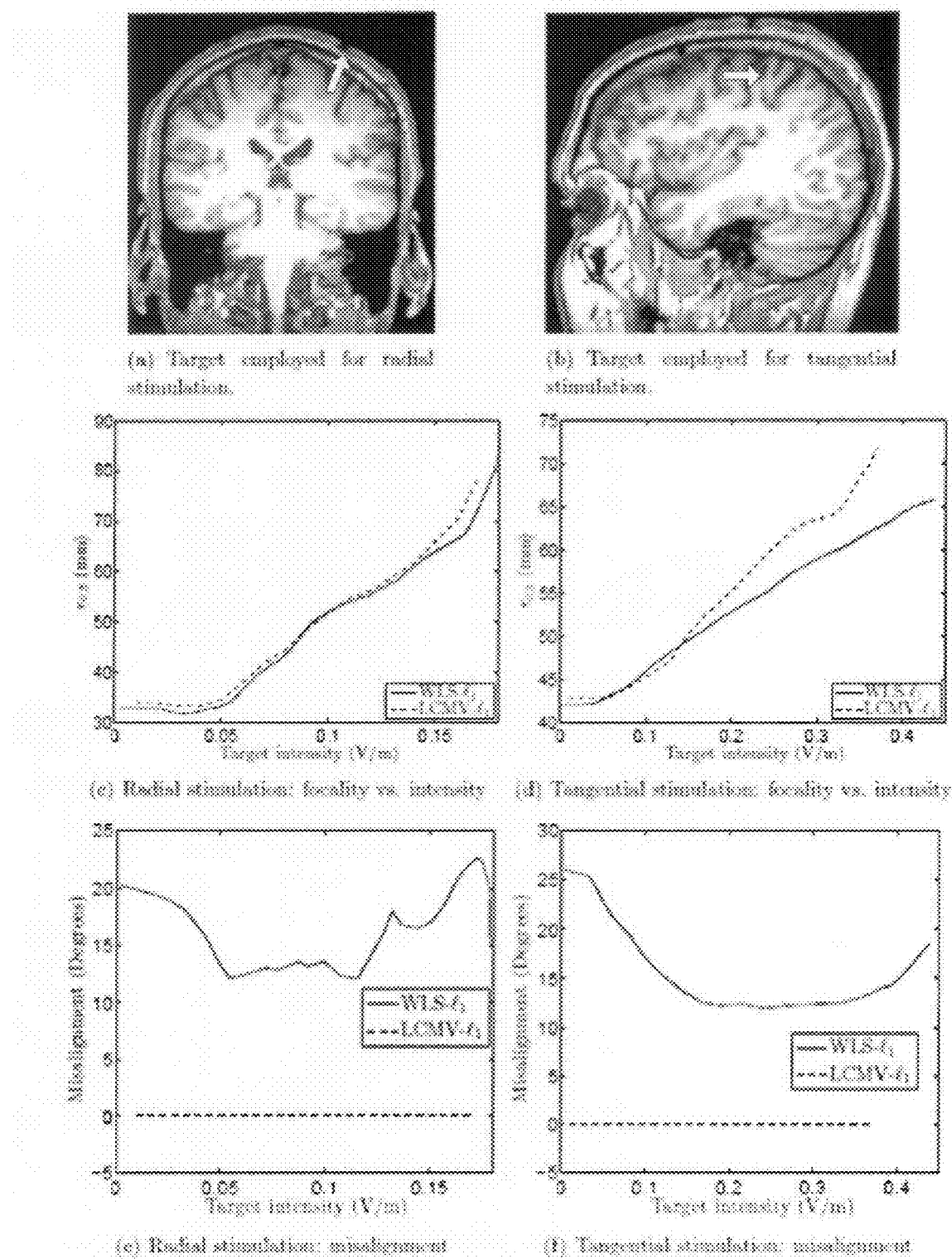
FIG. 13a illustrates a radial target of selected tissue.
FIG. 13b illustrates a tangential target of selected tissue
FIGS. 13c-f illustrate optimal current distribution as a function of desired orientation and criterion.

FIGS. 13c-d depict the intensity-focality curves yielded by both algorithms (LCMV and WLS) for a range of specified intensities: for the LCMV method, the intensity range varies from 0.01 V/m to 0.17 V/m in increments of 0.01 (fields beyond 0.17 V/m cannot be attained when limiting the total current to 2 mA. For the safety constrained WLS solution, the value of k values varies logarithmically form $10^{-4}$ to $10^1$ in 50 increments—these values resulted in a range of target intensities comparable to the LCMV intensity range. FIGS. 13e-f depict the misalignment in the field direction at the target for both methods.

In the case of radial stimulation, the two methods yield virtually equivalent focality across the obtained intensity range, with a slight separation in r0.5 occurring near 0.15 V/m When desiring tangential current flow, a more significant focality increase is attained by WLS above 0.15 V/m. Note that the LCMV feasible range is much broader (up to 0.37 V/m) in the tangential case than that of the radial target (0.17 V/m). Moreover, the WLS scheme yields intensities significantly beyond the LCMV feasible range with tangential stimulation. Note that while the WLS problem is feasible for all target intensities, the achievable intensity is of course limited by the safety constraints. From FIG. 13f, it is noted that the error in WLS field direction begins to rise sharply at approximately the intensity at which LCMV becomes infeasible: the optimization algorithm is limited in its degrees of freedom, and thus resorts to a greater angular mismatch in order to attain the desired target intensity.

It has thus been found that irrespective of the optimization algorithms used or the desired field direction, as the achievable intensities increase, the fields become more broadly distributed.

It has further been found that intensity and focality can be substantially improved over conventional approaches. To quantify the benefits of optimizing the applied currents and to establish an upper bound on achievable intensity and focality, a cortical target is used with both radial (FIG. 14a) and tangential stimulation (FIG. 15a). The half-max radii and the feasible target intensities are computed for a range of electrode montages and optimization criteria: simulated large pad electrodes (5 electrodes of same polarity), two "ad hoc" small electrode arrangements (4×1 or bipolar), and small electrode arrays optimized for focality with the $1_1$ norm constraint LCMV-$1_1$, optimized for focality without the safety constraint LCMV, and optimized for intensity irrespective of focality (max intensity).

Figure 14:
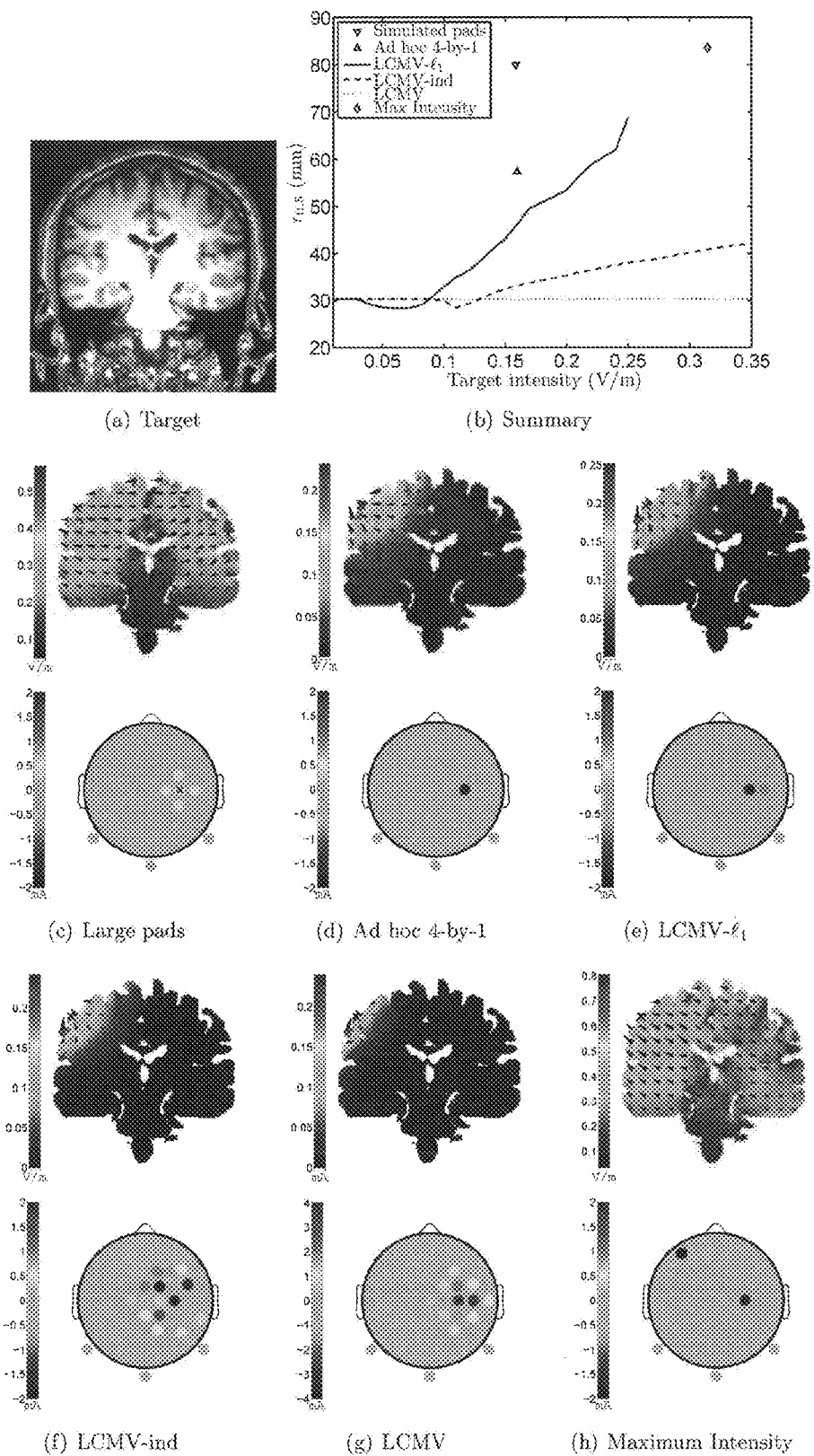
FIGS. 14a-h illustrate focality-intensity trade-offs.
Figure 15:
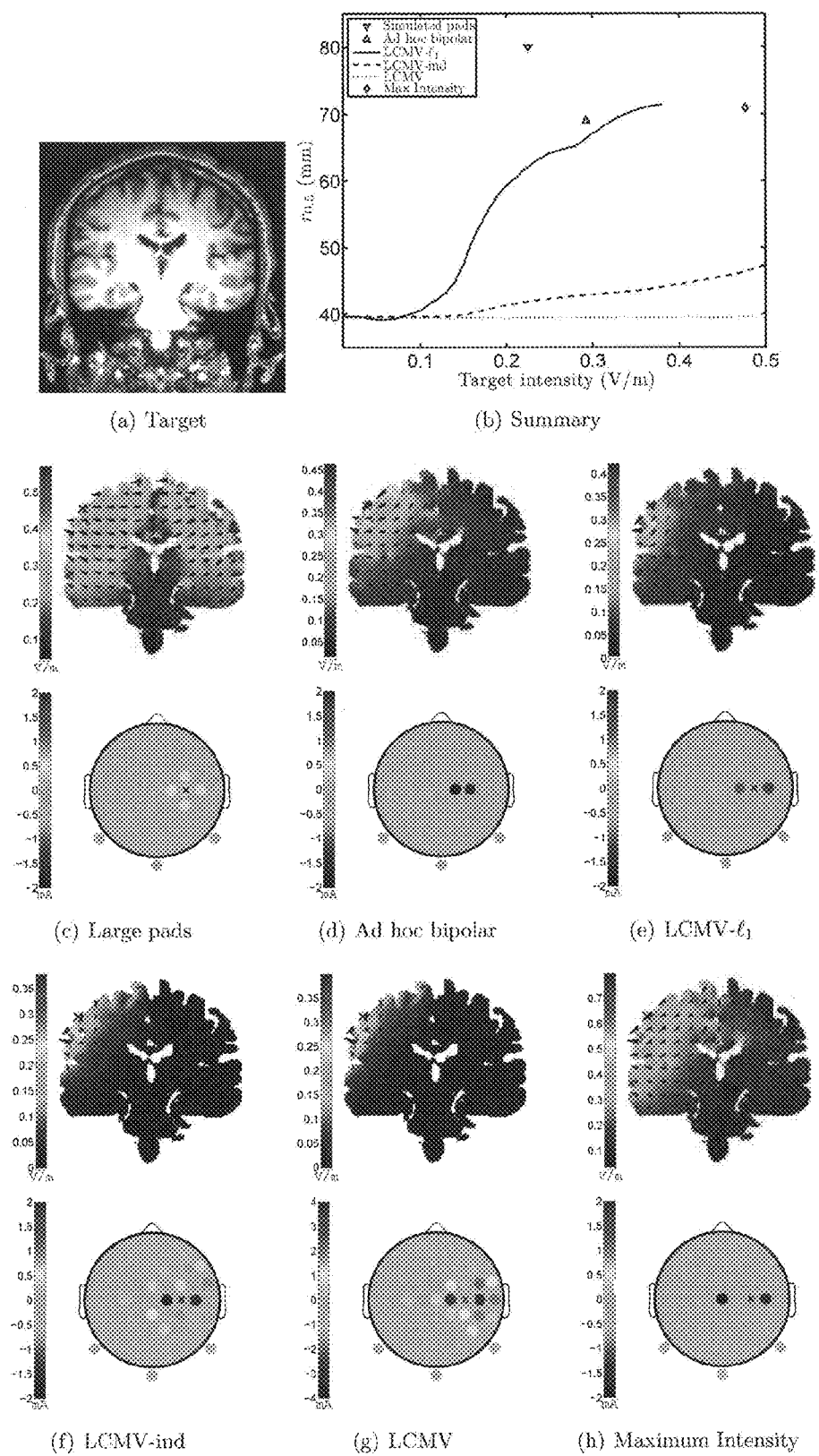
FIGS. 15a-h illustrate focality-intensity trade-offs.

FIGS. 14b and 15b depict the focality-intensity curves for the radial and tangential directions, respectively. Additionally, the coronal slice of the electric fields and optimal current distributions for all six schemes in FIGS. 14c-h (radial) and 15c-h (tangential)—for all focality optimized schemes, the coronal slices are shown for a target intensity of 0.16 V/m (0.23 V/m) in the radial (tangential) case.

In a further example, radial fields with the target underneath the electrode were also examined. Beginning with the radial case, it is noted that with the simulated pad montage, the field intensity at the target is 0.16 V/m with a half-max radius of 80 mm. Meanwhile, the ad hoc 4×1 configuration attains the same target intensity with half radius of 57 mm. It is further noted that the benefits of optimizing for focality become readily apparent, as the LCMV scheme achieves field intensities of up to 0.25 V/m, while maintaining a half-max radius of less than 69 mm. At the intensity attained by the simulated pad and ad hoc schemes (0.16 V/m), the LCMV method yields a 80% improvement in focality over the pads and 47% over the ad hoc scheme. The improvement is the percentage decrease in the volume containing half of the electric field.

Due to the increased degrees of freedom, the LCMV with currents constrained at each electrode exhibited excellent focality-intensity trade-off: r0.5 of 40 mm at 0.3 V/m. The LCMV method with unconstrained currents achieved a half-max radius of only 30 mm.

Referring to FIG. 14g, it is noted that the unconstrained solution resembles a "spherical sinc" function, with rings of alternating polarity centered over the target.

It is further noted that the LCMV solution (FIG. 14e) is a non-trivially modified version of the ad-hoc 4×1, with the difference being the location and the magnitude of the return electrodes. This slight difference accounts for a significant reduction in half-max radius. Thus the benefits of performing patient-specific optimization of the applied currents are apparent: the nominal 4×1 arrangement is only an approximation to the ideal solution (the unconstrained LCMV) and the idiosyncrasies of patient anatomy are indispensable to the computation of the maximally focal configuration (i.e., which electrodes to use as the returns, and how much current to pass through them).

The maximum intensity scheme yields a target intensity of 0.31 V/m representing a 97% (98%) improvement in achieved target intensity over the simulated pad (ad hoc 4×1) montage, while using the same amount of input current. From FIG. 14h, it is apparent to one of skill in the art that any attempt to maximize target intensity compromises focality, and the intensity optimized configuration takes the form of a "semi-distant" bipolar, with the stimulating electrode placed directly over the target. Due to the lack of symmetry in the montage, the resulting electric field lacks focality and leads to the introduction of several "hot spots." The optimization scheme of the present invention serves to identify the most intense bipolar configuration based on individual patient anatomy, the safety constraint, and the desired field orientation.

With regard to tangential fields with the target between electrodes, FIG. 15b details the focality-intensity trade-off in the case of tangential stimulation. In this example, the simulated pad and ad hoc bipolar montages attain target intensities of 0.23 and 0.29 V/m and half-max radii of 80 and 69 mm, respectively. At 0.23 V/m the $1_1$ norm constrained solution yields an improvement of 52% in focality over simulated pad scheme. Moreover, the improvement over the ad hoc bipolar montage at 0.29 V/m is 12%. The reduced improvement in focality compared to the radial case may be attributed to the fact tangential stimulation leads to larger target intensities—hence there are fewer degrees of freedom available to the optimization schemes, and thus only moderate gains in focality are observed.

The individual $1_1$ constrained and unconstrained LCMV solutions yield substantial improvements over conventional methods, with the half-max radius not exceeding 45 mm at 0.29 V/m.

In terms of target intensity, the maximum intensity scheme yields a target intensity of 0.48 V/m, representing an improvement of 63% and 112%, respectively, over the simulated pad and ad hoc bi polar montages. The maximally intense montage is bipolar with the pair of electrodes arranged in the direction of the desired orientation, and the target resting between the electrodes. Hence the optimization role is not in determining amount of current injected, but rather the location of the bipolar montage.

Reduced or Limited Number of Electrodes and/or Current Sources

The optimization examples described above utilize a larger number of electrodes, and assumes there are N electrodes and N−1 current sources. For the purpose of optimization it is desirable to have a large number of electrodes with a dense and comprehensive coverage of the head and distant electrodes. In FIG. 3 for instance 91 electrode positions are shown (many more are possible). In practice however the optimal solutions require significant currents only in a relatively small number of these electrodes (see FIG. 9 described above).

In addition, the hardware to implement these solutions will be typically limited in the number of independent current sources (typical values may be 4, 8, 16, etc.). Equally important, placing electrodes, gel application and ensuring proper contact becomes more cumbersome as the number of electrodes increases (even if an electrode cap with predefined locations is used).

Thus there is a need to obtain approximations to the optimal solution given a limited number of electrodes and/or a limited number current source channels. Once an optimal solution with N electrodes and N−1 current sources has been found one can consider how to approximate these optimal solutions with fewer electrodes or fewer channels.

In embodiments of the present invention, a method is presented for selecting electrodes and wiring diagram with the available independent current sources to achieve a good approximation to the optimal solutions for N electrodes.

Figure 16:
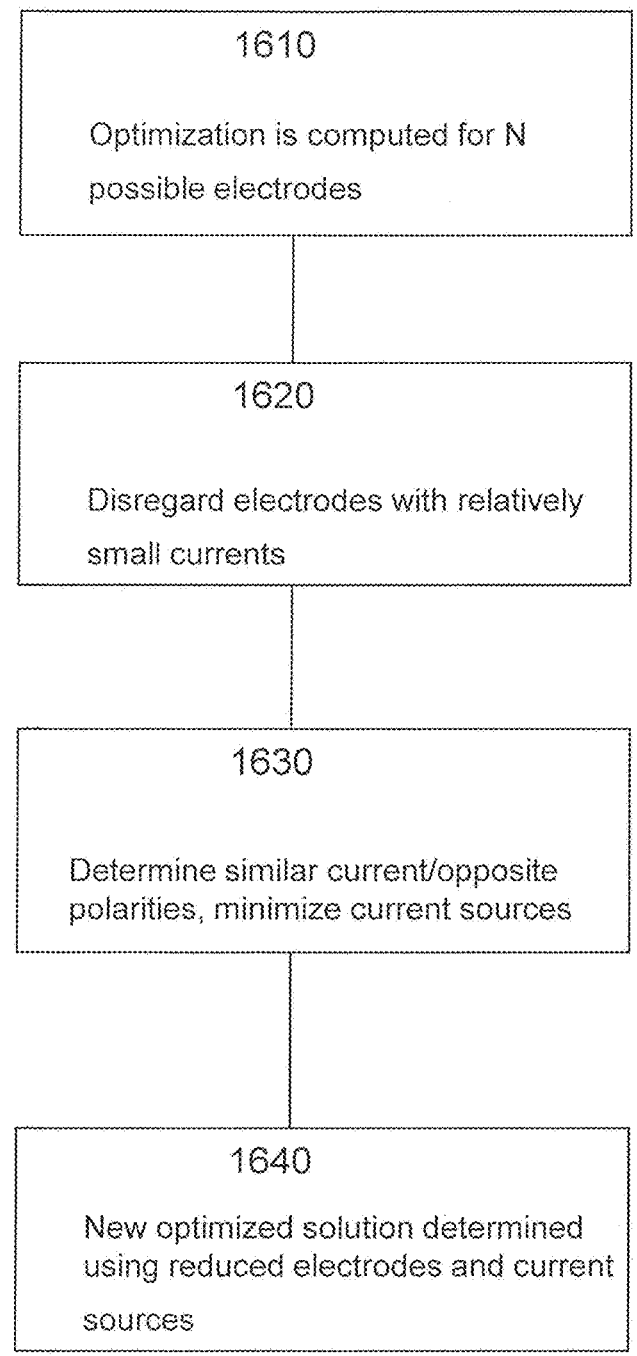
FIG. 16 illustrates a method of optimizing electrode configurations and criterion.

Referring to FIG. 16, the method 1600 comprises step 1610 in which optimization is computed for current source intensity and polarity on a large number N of potential electrode locations placed according to a conventional electrode placement system (such as the 10-10 system) and using N−1 independent current sources as described above (all sources share one electrode). Assume that in practice only M electrodes and K current sources are available, where M<N and/or K<N−1.

Next step 1620 ignores electrodes with small currents and selects electrode locations M with relatively large currents. Due to the sparseness constraint in the optimization, many of the potential electrode locations carry little or no current in the optimal solutions. One can simply ignore all those electrode locations with small currents and thus drastically reduce the number of required electrodes and current sources. It has been found that solutions with less than 20 electrodes (M<20) are sufficient in most practical examples. Thus, while N during the optimization may be very large (more than 100 perhaps) in practice only a small subset (M) of these is really needed (M<N). One should therefore think of the N electrode locations only as potential locations to be considered during optimization. For the actual location one should pick the M locations that carry the largest current (in absolute value).

At step 1630, electrodes with relatively similar or the same current values but opposite polarity are identified. Optimal solutions as described above were obtained with a simple wring diagram where one lead of all the N−1 current sources were connected to a single reference electrode while the other lead was each connected to a separate electrode, thus resulting in N electrodes total (one is common to all current sources). If the limitation is the number of current sources K this would mean that one can pick at most M=K+1 electrode locations. This may be limiting in cases that K is small (say K=4) and the optimal solutions requires more than 5 electrodes with non-zero currents. However, this wiring diagram is not the only way to connect electrodes to the available current sources. One could also connect the two leads of an independent current source to two separate electrodes (not connected to any other current source). The limitation in doing this is that those two electrodes are now constraint to carry the same current with opposite polarity in each.

To increase the number of nonzero-current electrodes, M, for a fixed number of current sources, K, one can search for electrodes in the optimal solution which have similar magnitude but opposing polarity. Each of these two electrodes can then be connected to a single current source. By doing so one can increase the number of non-zero-current electrodes and achieve an approximate optimal solution with a smaller number of current sources. For this replacement we searched electrode pairs for which the sum of current is approximately zero. In this same fashion one can search for three electrodes for which total current is approximately zero in the optimal solution and connect them to two current sources that share one electrode. Thus, if the number of current sources is limited one can search in the optimal solution first for pairs, then triplets, then quadruplets, etc. of electrodes that have approximately zero current in total and wire them accordingly to one current source, two current sources, three current sources, etc. Since each of these configurations achieves approximately the same currents as the original wiring diagram these are still nearly optimal solutions with a smaller number of required current sources.

At step 1640 a new optimal solution is computed using M electrodes and K sources of current. Optimization is accomplished using the methods described above. After this new wiring diagrams with M electrodes and K sources has been established (Step 2 and/or Step 3). The optimal solutions can be recomputed with this specific diagram. Each diagram corresponds to a linear combination of the existing solutions computed with individual pairs. Essentially the new "forward matrix" (see Dmochowski 2011) will have now K columns instead of N. And each column will be a linear combination of the pairs, triplets, quadruplets, etc of the corresponding columns in the original forward matrix. With this new matrix, optimization for current intensity can now be fine-tuned- to achieve an optimal solution with the new wiring diagram which is close to the optimal unconstrained case (in which many potential electrodes and channels were available).

Thus step 1620 aims to reduce the number of electrodes used from N to M in case that this should be the limiting factor. Step 1630 aims to reduce the number of required current sources from M to K in case that only K independent current sources are available. Step 1640 can be applied in either case (reduced M, reduced K, or both) and can also be omitted.

In general the problem is one of selecting the best subset of M actual electrode locations among a possible N electrode locations (M<N); and in addition selecting the best wiring diagram to connect K current sources to these M electrodes in case that K<M−1. The brute-force approach would be to compute the optimal current distribution for all possible combinations of electrode and sources. This combinatorial problem is prohibitive in computation time. Here we have proposed an effective four step solution that should find solutions that are close to the desired optimum. Other alternative strategies can be envisioned for those skilled in the art.

To be more specific, the problem is to find a partition of the N electrodes into T non-overlapping groups with each group containing ni electrodes where ni can be any positive integer, $N = \text{Sum}_{i=1 \ldots T} n_i$. Denote the set of electrodes in the i-th group with Ji, and the optimal current through each of the N electrodes with sj, s2, ..., sN. Then the problems of finding the best approximate wiring diagram of electrodes and sources with a limited number of M electrodes and K current sources can be expressed as finding the partition J1, J2, ..., JT that minimizes the approximation error:

$$\text{Error} = \text{Sum}_{i=1 \ldots T} (\text{Sum}_{j \text{ in } Ji} si)^2$$

subject to the constrains on electrodes $M = \text{sum}_{i=1 \ldots T} ni$, and the constrained on the number of current sources K=M−T. This is the error obtained if electrodes in Ji with ni=1 are dropped and ni >1 are connected with one shared electrode. Solving this general combinatorial problem to find the optimal partitioning is intractable. Here we describe one approximate solution to this problem, but having formulated it in its most general form, other approaches could also be envisioned.

Various embodiments of the invention find an efficient nearly optimal solutions to this problem as follows:

1. Current optimization is first done efficiently using a set of linear equations and constraints on a large set of N potential location with the full set of N−1 necessary current sources to effectively control all degrees of freedom.

2. Optimal solution can be implemented approximately with fewer than N electrodes, namely M<N, by dropping electrodes locations with the N−M smallest currents.

3. Optimal solution can be implemented approximately with fewer than M−1 current sources, namely K<M−1, by effectively wiring sources and currents as separate groups with n electrodes that share one electrode such these groups require n−1 independent current sources respectively.

4. After establishing this diagram it can be further optimized following the same optimization procedure as before with K degrees of freedoms and M electrodes.

Figure 17:
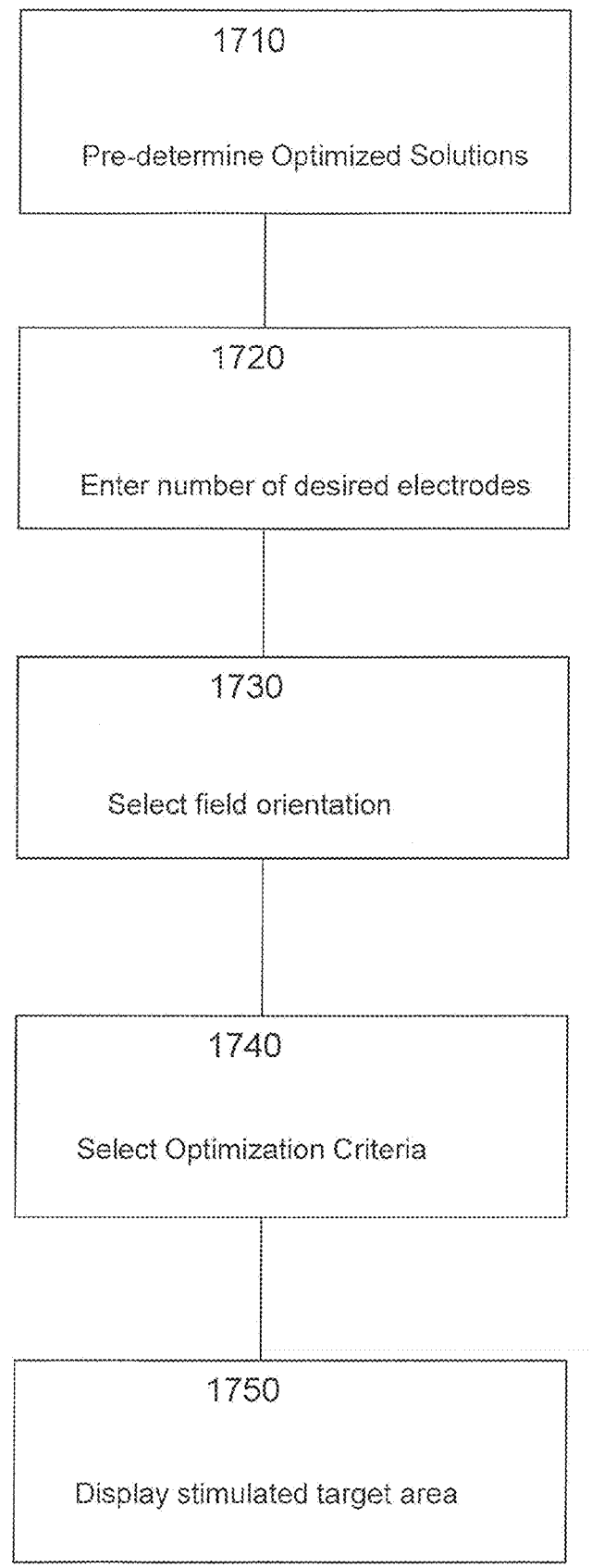
FIG. 17 illustrates a flow chart of an implementation of the present invention

Referring to FIG. 17, an implementation of a computer implemented methodology 1700 is provided, wherein optimized solutions for a multitude of predetermined electrode positions, current values, and locations within the brain are calculated and stored (1710) in a computer accessible library. Via a user interface, a user selects the number of desired electrodes (1720) (e.g., 2, 4, 6, 8, 10, 12, 14, 16, 18, 20, 22, 24 or more). Next the field orientation is selected by the user (1730). The field orientation can include 10 or more different orientations including: radial, radial in, radial out, posterior, posterior left, posterior right, anterior, anterior left, anterior right, right and left. Other orientations are possible. The user also inputs the optimization criteria, (1740), which can include Maximum Intensity and Maximum Focality. With the desired number of electrodes, field orientation and optimization criteria determined, the use can access predetermined optimized solutions and a visual representation of the electrode location and stimulated target area can be displayed 1750. Target areas of the brain are identified using the Talairach Coordinate System, as known in the art. Using a GUI interface of various brain locations, the user is able to identify new target areas, and new optimized solutions from the input criteria and the predetermined solution library.

Embodiments of the subject matter and the operations described in this specification can be implemented in digital electronic circuitry, or in computer software, firmware, or hardware, including the structures disclosed in this specification and their structural equivalents, or in combinations of one or more of them. Embodiments of the subject matter described in this specification can be implemented as one or more computer programs, i.e., one or more modules of computer program instructions, encoded on computer storage medium for execution by, or to control the operation of, data processing apparatus. Alternatively or in addition, the program instructions can be encoded on an artificially-generated propagated signal, e.g., a machine-generated electrical, optical, or electromagnetic signal, that is generated to encode information for transmission to suitable receiver apparatus for execution by a data processing apparatus. A computer storage medium can be, or be included in, a computer-readable storage device, a computer-readable storage substrate, a random or serial access memory array or device, or a combination of one or more of them. Moreover, while a computer storage medium is not a propagated signal, a computer storage medium can be a source or destination of computer program instructions encoded in an artificially-generated propagated signal. The computer storage medium can also be, or be included in, one or more separate physical components or media (e.g., multiple CDs, disks, or other storage devices).

The operations described in this specification can be implemented as operations performed by a data processing apparatus on data stored on one or more computer-readable storage devices or received from other sources.

The term "data processing apparatus" encompasses all kinds of apparatus, devices, and machines for processing data, including by way of example a programmable processor, a computer, a system on a chip, or multiple ones, or combinations, of the foregoing The apparatus can include special purpose logic circuitry, e.g., an FPGA (field programmable gate array) or an ASIC (application-specific integrated circuit). The apparatus can also include, in addition to hardware, code that creates an execution environment for the computer program in question, e.g., code that constitutes processor firmware, a protocol stack, a database management system, an operating system, a cross-platform runtime environment, a virtual machine, or a combination of one or more of them. The apparatus and execution environment can realize various different computing model infrastructures, such as web services, distributed computing and grid computing infrastructures.

A computer program (also known as a program, software, software application, script, or code) can be written in any form of programming language, including compiled or interpreted languages, declarative or procedural languages, and it can be deployed in any form, including as a stand-alone program or as a module, component, subroutine, object, or other unit suitable for use in a computing environment. A computer program may, but need not, correspond to a file in a file system. A program can be stored in a portion of a file that holds other programs or data (e.g., one or more scripts stored in a markup language document), in a single file dedicated to the program in question, or in multiple coordinated files (e.g., files that store one or more modules, sub-programs, or portions of code). A computer program can be deployed to be executed on one computer or on multiple computers that are located at one site or distributed across multiple sites and interconnected by a communication network.

The processes and logic flows described in this specification can be performed by one or more programmable processors executing one or more computer programs to perform actions by operating on input data and generating output. The processes and logic flows can also be performed by, and apparatus can also be implemented as, special purpose logic circuitry, e.g., an FPGA (field programmable gate array) or an ASIC (application-specific integrated circuit).

Processors suitable for the execution of a computer program include, by way of example, both general and special purpose microprocessors, and any one or more processors of any kind of digital computer. Generally, a processor will receive instructions and data from a read-only memory or a random access memory or both. The essential elements of a computer are a processor for performing actions in accordance with instructions and one or more memory devices for storing instructions and data. Generally, a computer will also include, or be operatively coupled to receive data from or transfer data to, or both, one or more mass storage devices for storing data, e.g., magnetic, magneto-optical disks, or optical disks. However, a computer need not have such devices. Moreover, a computer can be embedded in another device, e.g., a mobile telephone, a personal digital assistant (PDA), a mobile audio or video player, a game console, a Global Positioning System (GPS) receiver, or a portable storage device (e.g., a universal serial bus (USB) flash drive), to name just a few. Devices suitable for storing computer program instructions and data include all forms of non-volatile memory, media and memory devices, including by way of example semiconductor memory devices, e.g., EPROM, EEPROM, and flash memory devices; magnetic disks, e.g., internal hard disks or removable disks; magneto-optical disks; and CD-ROM and DVD-ROM disks. The processor and the memory can be supplemented by, or incorporated in, special purpose logic circuitry.

To provide for interaction with a user, embodiments of the subject matter described in this specification can be implemented on a computer having a display device, e.g., a CRT (cathode ray tube) or LCD (liquid crystal display) monitor, for displaying information to the user and a keyboard and a pointing device, e.g., a mouse or a trackball, by which the user can provide input to the computer. Other kinds of devices can be used to provide for interaction with a user as well; for example, feedback provided to the user can be any form of sensory feedback, e.g., visual feedback, auditory feedback, or tactile feedback; and input from the user can be received in any form, including acoustic, speech, or tactile input. In addition, a computer can interact with a user by sending documents to and receiving documents from a device that is used by the user; for example, by sending web pages to a web browser on a user's client device in response to requests received from the web browser.

Embodiments of the subject matter described in this specification can be implemented in a computing system that includes a back-end component, e.g., as a data server, or that includes a middleware component, e.g., an application server, or that includes a front-end component, e.g., a client computer having a graphical user interface or a Web browser through which a user can interact with an implementation of the subject matter described in this specification, or any combination of one or more such back-end, middleware, or front-end components. The components of the system can be interconnected by any form or medium of digital data communication, e.g., a communication network. Examples of communication networks include a local area network ("LAN") and a wide area network ("WAN"), an inter-network (e.g., the Internet), and peer-to-peer networks (e.g., ad hoc peer-to-peer networks).

The computing system can include clients and servers. A client and server are generally remote from each other and typically interact through a communication network. The relationship of client and server arises by virtue of computer programs running on the respective computers and having a client-server relationship to each other. In some embodiments, a server transmits data (e.g., an HTML page) to a client device (e.g., for purposes of displaying data to and receiving user input from a user interacting with the client device). Data generated at the client device (e.g., a result of the user interaction) can be received from the client device at the server.

While this specification contains many specific implementation details, these should not be construed as limitations on the scope of any inventions or of what may be claimed, but rather as descriptions of features specific to particular embodiments of particular inventions. Certain features that are described in this specification in the context of separate embodiments can also be implemented in combination in a single embodiment. Conversely, various features that are described in the context of a single embodiment can also be implemented in multiple embodiments separately or in any suitable subcombination. Moreover, although features may be described above as acting in certain combinations and even initially claimed as such, one or more features from a claimed combination can in some cases be excised from the combination, and the claimed combination may be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system components in the embodiments described above should not be understood as requiring such separation in all embodiments, and it should be understood that the described program components and systems can generally be integrated together in a single software product or packaged into multiple software products.

Thus, particular embodiments of the subject matter have been described. Other embodiments are within the scope of the following claims. In some cases, the actions recited in the claims can be performed in a different order and still achieve desirable results. In addition, the processes depicted in the accompanying figures do not necessarily require the particular order shown, or sequential order, to achieve desirable results. In certain implementations, multitasking and parallel processing may be advantageous.

All references and publications disclosed or discussed herein are incorporated by reference in their entirety.

What is claimed is:

1. A method performed by data processing apparatus, the method comprising:
    forming a first array of electrodes;
    optimizing a plurality of electrode parameters within the first array of electrodes to achieve a desired physiological response;
    identifying one or more electrodes within the optimized first array that have relatively low current compared to the remaining electrodes in the first array;
    identifying two or more electrodes within the optimized first array that have relatively equal current with opposite polarity;
    forming a second array of electrodes based on the first array of electrodes by at least one of removing the identified low current electrodes from the first array or electrically connecting the identified two or more electrodes with relatively equal current and opposite polarity to the same current source, wherein the number of electrodes in the second array is less than the number of electrodes in the first array;
    optimizing a plurality of electrode parameters with the second array of electrodes to achieve a desired physiological response.

2. The method of claim 1 wherein the first array has N electrodes, the second array has M electrodes, wherein M is less than N, and the second array has K current sources, wherein K is less than M−1.

3. The method of claim 1 wherein the first array of electrodes includes electrodes in a standard electrode placement system.

4. The method of claim 3 wherein the standard system of electrode placement is the 10/10 system, the 10/20 system, the concentric system, or the geodesic system.

5. The method of claim 3 wherein the second array of electrodes comprises a constraint number of electrodes less than the number of electrodes in the first array.

6. The method of claim 1 wherein the first array is optimized for at least one of focality or intensity of the physiological response.

7. The method of claim 1 wherein the physiological response is determined from the electrical filed or current density induced within the tissue.

8. The method of claim 1 wherein optimizing the first and second arrays is done using optimization criteria formulated as a convex optimization problem and solved with a least one of linearly constrained Least Squares minimization, weighted Least Squares, Linearly Constrained Minimum Variance, maximum magnitude with a linear-norm constrains, or a convex optimization technique.

9. The method of claim 1 wherein the physiological response is at a specified location of brain tissue subjected to a defined orientation of the electrical field induced by the plurality of electrodes in the first or second arrays.

10. The method of claim 1, wherein the second array of electrodes is formed by both removing the identified low current electrodes from the first array and electrically connecting the identified two or more electrodes with relatively equal current and opposite polarity to the same current source.

11. The method of claim 1, wherein the second array of electrodes is formed by removing the identified low current electrodes from the first array, and the method further comprises:
    identifying two or more electrodes within the optimized second array that have relatively equal current with opposite polarity; and
    electrically connecting the two or more electrodes identified within the optimized second array with relatively equal current and opposite polarity to the same current source.

* * * * *